(12) United States Patent
Bureau

(10) Patent No.: US 9,863,052 B2
(45) Date of Patent: Jan. 9, 2018

(54) FORMATION OF ORGANIC ELECTRO-GRAFTED FILMS ON THE SURFACE OF ELECTRICALLY CONDUCTIVE OR SEMI-CONDUCTIVE SURFACES

(71) Applicant: ALCHIMEDICS, Grenoble (FR)

(72) Inventor: Christophe Bureau, Uriage (FR)

(73) Assignee: ALCHIMEDICS, Grenoble (FR)

( * ) Notice: Subject to any disclaimer, the term of this patent is extended or adjusted under 35 U.S.C. 154(b) by 467 days.

(21) Appl. No.: 14/301,476

(22) Filed: Jun. 11, 2014

(65) Prior Publication Data

US 2015/0112426 A1 Apr. 23, 2015

Related U.S. Application Data

(62) Division of application No. 11/711,849, filed on Feb. 28, 2007, now Pat. No. 8,784,635.

(60) Provisional application No. 60/776,929, filed on Feb. 28, 2006.

(51) Int. Cl.

| A61F 2/82 | (2013.01) |
|---|---|
| A61L 31/10 | (2006.01) |
| A61L 31/14 | (2006.01) |
| C09D 5/44 | (2006.01) |
| C25D 9/02 | (2006.01) |
| C25D 13/18 | (2006.01) |
| C25D 7/12 | (2006.01) |
| C09D 5/24 | (2006.01) |

(52) U.S. Cl.
CPC ............... *C25D 7/12* (2013.01); *A61F 2/82* (2013.01); *A61L 31/10* (2013.01); *A61L 31/14* (2013.01); *C09D 5/24* (2013.01); *C09D 5/4476* (2013.01); *C25D 9/02* (2013.01); *C25D 13/18* (2013.01); *A61F 2210/0076* (2013.01); *A61L 2420/04* (2013.01); *A61L 2420/08* (2013.01); *C09D 5/4407* (2013.01); *C09D 5/448* (2013.01); *C09D 5/4419* (2013.01); *C09D 5/4423* (2013.01)

(58) Field of Classification Search
None
See application file for complete search history.

(56) References Cited

U.S. PATENT DOCUMENTS

| 3,880,956 | A | * | 4/1975 | Skoultchi | ................... | C09J 4/00 523/176 |
| 2005/0255631 | A1 | * | 11/2005 | Bureau | ................... | C08J 5/121 438/106 |

FOREIGN PATENT DOCUMENTS

WO    WO 2004018548 A2  *  3/2004    .............. C08J 5/121

OTHER PUBLICATIONS

Bureau, et al., Comments on "The Electroreduction of Acrylonitrile: A New Insight into the Mechanism" by Mertens et al., *Macromolecules* 1997, 30, pp. 333-336.
Bureau, et al., Electrochemistry as a Tool to Monitor Lewis Acid-Base Reactions between Methacrylonitrile and Metallic Surfaces: A Theoretical and Experimental Proposal, *J. Adhesion*, 1996, vol. 58, pp. 101-121.
Bureau, C., Polymerization reaction coupled to the charge transfer: propagation versus termination as a source of permanent travelling waves and multi-peak voltammograms, *Journal of Electroanalytical Chemistry* 000 (1999), pp. 1-14.
Bureau, et al., Synthesis and Structure of Polymer/Metal Interfaces: a Convergence of Views between Theory and Experiment, *Journal of Surface Analysis*, vol. 6, No. 2 (1999), pp. 159-170.
Palacin, et al., Molecule-to-Metal Bonds : Electrografting Polymers on Conducting Surfaces, *ChemPhysChem* 2004, 5, pp. 1468-1481.
Zhang, et al., Studies of Arenediazonium Salts as a New Class of Electropolymerization Initiator, *Journal of Applied Polymer Science*, vol. 73, (1999), pp. 2265-2272.

* cited by examiner

*Primary Examiner* — Ramsey Zacharia
(74) *Attorney, Agent, or Firm* — Finnegan, Henderson, Farabow, Garrett & Dunner, L.L.P.

(57) ABSTRACT

The invention relates to a method for grafting an organic film onto an electrically conductive or semiconductive surface by electro-reduction of a solution, wherein the solution comprises one diazonium salt and one monomer bearing at least one chain polymerizable functional group. During the electrolyzing process, at least one protocols consisting of an electrical polarization of the surface by applying a variable potential over at least a range of values which are more cathodic that the reduction or peak potential of all diazonium salts in said solution is applied.
The invention also relates to an electrically conducting or semiconducting surface obtained by implementing this method.
The invention further relates to electrolytic compositions.

89 Claims, 5 Drawing Sheets

FORMATION OF ORGANIC ELECTRO-GRAFTED FILMS ON THE SURFACE OF ELECTRICALLY CONDUCTIVE OR SEMI-CONDUCTIVE SURFACES

This is a division of application Ser. No. 11/711,849, filed Feb. 28, 2007, and claims the benefit of U.S. Provisional Application No. 60/776,929, filed Feb. 28, 2006, all of which are incorporated herein by reference.

CROSS-REFERENCE TO RELATED APPLICATION

This application is based on and claims the benefit of U.S. Provisional Application Ser. No. 60/776,929, filed Feb. 28, 2006. The entire disclosure of this Provisional application is relied upon and incorporated by reference herein.

The present invention is related to the field of organic surface coatings, said coatings being in the form of organic films on the surface. More specifically, it is related to the use of solutions suitably selected in order to allow the simple and reproducible formation of organic films by electro-chemical grafting—or electro-grafting—on a surface or a portion or portions of a surface which is (are) electrically conductive or semiconductive.

There are several techniques in the prior art to achieve the deposition of thin organic films on substrates, each one relying on a specific family or a class of precursor molecules. The process of formation of a coating by centrifugation or "spin coating", by immersion ("dip coating") or by vaporization ("spray coating") do not necessitate that the molecules being deposited have any particular affinity with the substrate of interest. Indeed, the mere process itself enables one to obtain a film on the surface, the cohesion of which is primarily due to the cohesion energy of the film, which can be reinforced by a post-treatment, for example by cross-linking, in order to improve its stability.

It is possible to increase the stability of the interface in these processes by using specific molecules which can undergo self-assembly on the surface. These molecules are known in the prior art as those giving rise to self-assembled monolayers or SAMs (Ulman A., "Year introduction to ultrathin organic films from Langmuir-Blodgett films to coil-assembly", 1991, Boston, Academic Press). There is usually no straightforward relationship between self-assembly, which essentially describes lateral interaction between adjacent molecules which are in a more or less close packing arrangement, and the fact that the overall "close-packed" layer has an affinity for the underlying surface. In many examples, such close packed monolayers have also been obtained with mono- or di-functional molecules, one end of which has a strong affinity for the surface: monolayer brushes are obtained at high density of molecules on the surface, even if these molecules have limited lateral interaction and—as such—cannot be considered as self-assembling. Even though the underlying mechanism accounting for the formation of a monolayer is different in the two cases, there seems to be a trend to designate as SAMs ultra-thin layers—possibly monolayers—that are actually formed by strong bonding on the surface, at high density of bonds on the surface. "True" SAMs, with only lateral interactions, point to little (if any) improvement of the adhesion at the interface, while mono- or di-functional molecules added to a dip or spray formulation can have a definite effect by strengthening the interface via anchoring points. Since the bonding of said mono- or di-functional molecules is important in this strengthening, one will have to consider the precursor-surface couple as a whole. As an example, sulphur containing molecules are known to have a strong affinity for gold, silver or copper, tri-halogeno silanes for oxides like silica or alumina, polyaromatic molecules for graphite or the carbon nanotubes . . . etc. In all the cases, the formation of film relies on a specific physico-chemical interaction, which may go to chemical reaction, between a part of the molecular precursor (the sulphur atom in the case of thiols for example) and certain "receptor" sites on the surface. One can obtain, in favorable cases, ultra-thin layers (<10 nm) at ambient temperature by spray or dip.

However, since the formation of the interface bonds is very much related to both the precursor and the surface, favorable couples are actually very limited to almost "ideal" situations. Silanes give rise to interface Si—O—Si interface bonds, which are probably among the strongest in chemistry, but these bonds are readily hydrolyzed at room temperature in water. Thiol give rise to fairly strong bonds on gold surfaces, but readily desorbs at 60° C. or in a good solvent at room temperature, or else as soon as they are in contact with a liquid medium containing an oxidant of the thiol group. As a whole, the possibilities to use self-assembly and/or mono- or di-functional molecules to obtain good adherence onto metals and/or semiconducting surface are very limited. This is even more so when said surfaces are being obtained by some specific techniques such as sputtering or by physical or chemical vapor deposition, as the said surface obtained is usually non stoichiometric and of a non standard composition.

Nevertheless, when favorable cases can be considered, these techniques of spray and dip are very versatile, applicable to most types of surfaces, and fairly reproducible. However, they do not promote any effective bonding between film and the substrate (apart from a mere physical absorption), and the thickness of the films is hardly controllable, in particular when ultra-thin layers are the target (<20 nanometers). Moreover, the techniques of spin coating allow uniform deposits only when the surface to be coated is primarily plane (see French patent application FR2843757). The quality of films (in terms of homogeneity and conformality) obtained by the spray coating are related to the wetting of the substrate by the sprayed liquid, since the deposit becomes essentially filmogenic only when the droplets of liquid coalesce on the surface. Thus, for a given polymer, there are generally only a few organic solvents able to give satisfactory results in terms of control of both the homogeneity and the conformality of the coating.

Other techniques of formation of an organic coating on the surface of a support, such as the plasma deposition described for example in the articles of Konuma M., "Film deposition by plasma techniques", (1992) Springer Verlag, Berlin, and of Biederman H. and Osada Y., "Plasma polymerization processes", 1992, Elsevier, Amsterdam, or photochemical activation, rely on similar principle: generate an unstable derivative of a precursor molecule in the vicinity of the surface, the evolution of which eventually leads to film formation on said surface. Plasma deposition usually does not require that the precursors have any particular chemical property; photo-activation requires the use of photosensitive precursors, the structure of which is modified under irradiation.

These techniques usually lead to the formation of adherent films on the treated surface, although it is generally difficult—if merely possible—to distinguish if this adhesion is due to a cross-linking of a film topologically closed around the object or to the actual formation of bonds at the interface between the film and the surface.

The electro-grafting of polymers is an alternative technique based on the formation of a polymer layer on a surface in situ, i.e. from a bath of precursors rather than from a pre-made polymer. The surface to be coated is polarized electrically, and serves as a polymerization initiator which provokes surface polymerization via propagation chain reactions (S. Palacin and Al, "Molecule-to-metal bonds: electrografting polymers on conducting surfaces", Chem Phys Chem, 2004, 10, 1468).

What is interesting is that the reaction of the polarized surface with the first monomer is a step creating a chemical bond which is then stabilized by the polymerization propagation: the presence of the film at the end of the process is thus a direct proof or footprint of the chemical bond which exists between the film and the surface. According to the reaction mechanism, there cannot be a polymer film on the surface if there is no charge transfer and bond formation with the first monomers.

Electron-poor "vinylic" molecules, i.e. bearing an electron-withdrawing functional group, like acrylonitriles, acrylates, vinylpyridines . . . are particularly adapted to this process, which proceeds via an anionic propagation mechanism.

The reaction mechanism of electro-grafting was in particular described in the articles of C. Bureau et al., Macromolecules, 1997, 30, 333; C. Bureau and J. Delhalle, Journal of Surface Analysis, 1999, 6(2), 159 and C. Bureau et al., Journal of Adhesion, 1996, 58, 101.

The growth of the polymer layer proceeds via anionic propagation in cathodic electro-grafting. This growth is stopped in particular by protons, and it was even shown that the content of protons constitutes the major parameter which controls the polymer formation in solution; the information obtained in the course of synthesis, in particular the shape and characteristics of the voltammograms recorded during the synthesis (see in particular the article of C. Bureau, Journal of Electroanalytical Chemistry, 1999, 479, 43).

Water traces, and more generally labile protons of protic solvents, constitute sources of protons prejudicial to the anionic growth of the polymeric chains, both in solution and on the surface. As described in patent FR2860523, it is however preferable—to optimize the thickness of the electro-grafted films—to perform the electro-grafting of vinylic monomers in a bath containing at least 50 ppm of water, and ideally approximately 1000 water ppm, that is to say in an electrolytic bath containing about as much water as the electrolyte support, if not more. This unexpected result comes from the fact that two types of polymerizations are in competition in electro-grafting: (i) the growth of the chains starting from an initiator on the surface, i.e. the growth coupled with the grafting itself; (ii) the chain growth resulting from the dimerisation of the desorbed radical anion (C. Bureau, Journal of Electroanalytical Chemistry, 1999, 479, 43): this growth is carried out in solution, independently of surface, and can give place to films if the local concentration of the said polymer formed in solution exceeds its local threshold of solubility in the vicinity of the said surface. This film is, in general, not adherent and can be eliminated from surface by simple rinsing with a good solvent of the polymer (in cases when the electro-grafting is performed in a good solvent of the polymer, it usually is not even visible in the final surface, which only bears the electro-grafted layer). The competition between these two reactions of polymerization is in general kinetically in favor of the reaction in solution, which is a homogeneous reaction, compared to the surface reaction, which is heterogeneous. In the vicinity of surface, the medium is impoverished in monomers especially because of the polymerization in solution, which "chokes" the polymerization resulting from the grafting. It is thought that the protons added in the reaction medium by water addition make it possible to limit this imbalance by "killing" the major reaction, i.e. the polymerization in solution, for the benefit of the surface reaction, by maintaining the local concentration in monomer in the vicinity of surface higher than in the total absence of water. This mechanism, which states that "more water is better", though rather counter-intuitive for an anion-driven polymerization, makes it possible to account for all observations, including the very peculiar voltammograms obtained in these "non-aprotic" modes of electro-grafting.

However, this mode is observed only for concentrations in protons not exceeding a few hundreds or a few thousands of ppm in water, above which the growth starting from surface itself is killed and there is no electro-grafted film formed on the surface. In practice, it is almost more difficult to maintain a solution with a water content given than to maintain it with a very low water content, as it is the case for example when the aforementioned solution is maintained in contact with freshly prepared molecular sieves.

All in all, if one can thus carry out chemical bonds on conducting or semiconductor substrates by electro-grafting of various precursors starting from organic solutions, there remains a difficulty to obtain, thanks to these reactions, such films starting from solutions that would be easy to prepare and control, because the subjacent reactional mechanisms (polymerization of the anion type) do not make it possible to work in solutions containing arbitrary water contents.

Until now, only salts of aryldiazonium allowed an approach of solution to this problem. Thus, as described for example in French patent application FR2804973, the electro-grafting of precursors such as aryldiazonium salts, which carry a positive charge, is carried out thanks to a reaction of cleavage after reduction of the cation, to give a radical which is chemically absorbed on surface. Just as in the case of the electro-grafting of polymers, the reaction of electro-grafting of aryldiazonium salts is electro-initiated and leads to the formation of chemical bonds of interface. Alternative to the electro-grafting of vinylic monomers, the electro-grafting of aryldiazonium salts does not require that a chemical reaction be coupled to the charge transfer to stabilize the chemically absorbed species, because this latter species is neutral electrically. The electro-grafting of aryldiazonium salts thus leads straightforwardly to a surface/aryl bond which is stable. It was shown, in particular in French patent application FR2829046, that aryldiazonium salts lead to very thin organic films which are conductive of electricity, and which can thus grow on themselves: once the grafting of a first aryl film is obtained on the initial surface via electro-cleavage+chemisorption, the film grows by electro-sustained reaction, i.e. a reaction in which more polymer film is formed as more current flows through the electrode. As a result, such films are usually more difficult to control, in particular as regards their thickness.

It was observed (cf: X. Zhang and J. P. Bell, Journal of Applied Polymer Science, 73, 2265, 1999) that the electroreduction of a solution containing an aryldiazonium salt and a vinylic monomer can lead to the formation of a polymeric film of the said monomer on the surface provided that the said polymer is insoluble in the solvent used for the electrosynthesis. One of the advantages of the mixtures of aryldiazonium and vinylic monomers, as claimed in this article, is that the polymer can be obtained by electrosynthesis without having to apply the high cathodic voltages required to achieve the electro-reduction of the vinylic monomer: it is sufficient to obtain the reduction of the aryldiazonium salts, which are used then as initiators of a radical type polymerization. Zhang et al. (op.cit.) indeed observe that by carrying out polarization at constant potential (−0.8 V/SCE) of an aqueous solution containing an aryldiazonium salt at a concentration of about $10^{-2}$ mol/l and of acrylamide, they do not observe the formation of any film on the surface of a steel coupon, but abundant formation of a polymer in solution. They interpret this data by arguing that polyacrylamide is water soluble. Conversely, they observe that by carrying out polarization at constant potential (−1.0 V/SCE) of an aqueous solution containing an aryldiazonium salt at a concentration of about $5.10^{-3}$ mol/l and of a mixture of acrylonitrile and methyl methacrylate with concentrations of 0.24 and 0.36 mol/l, respectively, they observe the formation of a whitish film on the surface of a similar steel coupon, which reveals a very thick film. After 30 minutes of electrolysis, the thickness of film is estimated to be 1 micrometer, which is significantly larger than what can be achieved by electro-grafting of the mere vinylic monomers. They interpret this result by indicating that the formed copolymer—the structure of which is identified by variable-angle reflection absorption infrared spectroscopy—is completely insoluble in water and has precipitated on surface.

These results are appealing for the skilled person who wishes to obtain polymeric films on metallic substrates. However, the reaction of grafting or strong bond formation, which constituted one of the outstanding characteristics of the reactions of electro-grafting, disappears under the operating conditions selected by Zhang et al., who obtain the formation of the film by precipitation on the surface.

The present invention reveals an operational mode in which it is possible to easily carry out an actual electro-grafting of a polymer starting from precursors solutions which are easy to prepare and control, in particular thanks to:

(i) a protocol of application of the electrode potential which forces the reaction of grafting;

(ii) the use of an electrolytic medium which is at least a good swellant of the formed polymer, or even a good solvent of the said polymer.

The objective of this invention is to propose a process enabling the electro-grafting, on all conducting or semiconducting substrates or on any such portion of a composite surface, of organic films, and in particular polymeric, having a thickness going from the nanometer to a few microns, and preferably from around 10 nanometers to 1 micron.

Such organic films can be useful either for their intrinsic properties, or as underlayers or interface layers for the fixing of further materials, if necessary, possibly by another means like dip coating, spray coating or spin coating.

As described in patent FR2843757, a good reinforcement of adhesion of a functional layer, for example organic, can be obtained thanks to a grafted organic underlayer—and in particular polymeric—when the latter has a thickness at least about a few tens or of a hundred nanometers: this length is of the order of the radius of gyration of the majority of known polymers, so that an underlayer being a thickness at least this length is theoretically sufficient to allow for the interdigitation of the polymer of the functional layer into the grafted underlayer, i.e. to allow the formation of at least one loop of polymer of the functional layer within the grafted underlayer. In short, it seems established that a better adhesion can be obtained with thin to ultra-thin underlayers provided they are grafted on surface, as compared to relatively thick layers like those described in the prior art.

As it is described in patent FR2837842, it can be interesting to even obtain electro-grafted polymer films which are not vinyl (polyethyleneglycol PEG, poly(dimethylsiloxane) PDMS . . . etc), of macromolecules which are not polymers (dextrane, proteins, ADN . . . etc), or of macro-objects which are not macromolecules (nanotubes of carbons, fullerenes, aggregates inorganic . . . etc). The same vinyl precursors as those described in patent FR2837842 can be used in the present invention, and one will use in all that follows the term of monomer or vinyl monomer without additional precision, being understood that the aforementioned monomer can be selected among all the types of precursors already listed in patent FR2837842.

The present invention relies on the fact that when one applies a time-dependent electrode potential protocol, provided that this protocol contains cathodic excursions at potentials which are higher than a certain threshold, with an electrode dipped in an electrolytic bath comprising at least a diazonium salt and at least one monomer, then one can obtain—after rinsing—the formation of an adherent polymeric film of the said monomer.

A first object of the invention is a method for grafting an organic film onto an electrically conductive or semiconductive surface by electro-reduction of a solution, comprising the following steps:

a) preparation of a solution containing at least one diazonium salt and one monomer bearing at least one chain polymerizable functional group, that are precursors of said organic film, b) electrolyzing said solution in an electrolysis cell using the conducting or semiconducting surface to be coated as working electrode and at least one counterelectrode, so as to result, by application of at least one protocol consisting of an electrical polarization of the surface by applying a variable potential over at least a range of values which are more cathodic that the reduction or peak potential of all diazonium salts in said solution, in a grafted coating of said organic film on said surface.

At least one protocol is advantageously applied in cyclic voltammetry scanning (CVS) mode.

In a at least one protocol, a variable working current is advantageously applied to the surface.

According to the present invention, the monomer is a compound bearing at least one chain polymerizable functional group. The polymerizable group can contain a variety of polymerizable moieties such as double bonds, cycles (polymerization by opening of the cycle), or functional groups. In a preferred embodiment, the monomer is a vinylic monomer. In an other preferred embodiment, the monomer is a polymerizable cyclic compound, such as lactones The threshold under consideration in the present invention is the reduction potential of the aryl diazonium in the solution.

As is detailed in examples below, an adherent film of poly-hydroxyethyl methacrylate (poly-HEMA) can be obtained upon voltametric scanning of a surface (stainless steel, TiN thin film, Nitinol) in a solution containing 4-nitrobenzenediazonium tetrafluoroborate at $10^{-2}$ mol/l and HEMA at 2 mol/l (solvent=DMF/water), over a potential range of −0.1 V/ECS to −1.2 V/ECS at a scanning rate of 100 mV/s. P-HEMA is a very hydrophilic polymer which is highly soluble in water: electrochemical impedance spectroscopy (EIS) data nevertheless show that the poly-HEMA layer obtained by the process of the present invention remains fully swollen by water and allows for ionic conduction. This brings a piece of evidence that this film has little crosslinking if any, and that its adhesion on the surface is a result of bond formation with the underlying metal. For this reason, we shall make use of the term electro-grafting of the polymer hereafter, even though it now refers to a grafting that is obtained by the electro-reduction of a solution containing both a monomer that can undergo propagation chain reaction and of a diazonium salt, the latter being preferably at low concentration.

It is a strong result of the present invention that the same process can also be applied to monomers that usually undergo anionic growth almost exclusively, such as monomers that can undergo ring opening polymerization, e.g. lactones such as ε-caprolactone or lactides such as lactic or glycolic acids. These monomers have in common with vinylics that they undergo propagation chain reaction, and may thus be described as "chain polymerizable" monomers but unlike the vinylics, they are know to be more—if not exclusively—prone to anionic growth.

Nevertheless, it is observed than upon voltammetric scanning polarization of a 316L stainless steel coupon in a water solution containing 4-nitrophenyl diazonium tetrafluoroborate at $10^{-2}$ mol/l and L-di-lactide at 0.5 mol/l, over a potential range of −0.2 V/ECS to −2.8 V/ECS, at a scanning rate of 100 mV/s, a film or polylactic acid (PLA), with a thickness of close to 1.1 µm, is formed on the surface of the coupon. The film withstands rinsing in water, even under sonication, which indicates that a strong adhesion through grafting could be obtained. This type of film is of high interest in the biomed as PLA is a biodegradable film.

Thus, one may consider that the present invention relies on the fact that when one applies a time-dependent electrode potential protocol, provided that this protocol contains cathodic excursions at potentials which are higher than a certain threshold, with an electrode dipped in an electrolytic bath comprising at least a diazonium salt and at least one monomeric compound, i.e. a molecular type compound bearing at least one chain polymerizable functional group, then one can obtain—after rinsing—the formation of an adherent polymeric film based on the said monomer.

The examples below illustrate the main advantages brought about by the use of the process of the present invention:

(i) the process can be applied to all electrically conductive and semiconductive surfaces such as 316L stainless steel, cobalt chromium alloys, titanium surface, titanium nitride . . . ;

(ii) the process allows for the versatile production of homopolymer layers with on demand properties: hydrophilic layers with HEMA (hydroxyethyl methacrylate) as the monomer, hydrophobic layers with BUMA (butyl methacrylate) as the monomer . . . ;

(iii) the process allows for the versatile production of co-polymer layers with on demand properties: hydrophilic to hydrophobic layers with co-polymers of varying ratio of BUMA and MPC (2-methacryloyloxyethyl phosphorylcholine) as the monomers . . . ;

(iv) the process allows for the versatile production of organic layers made of non vinylic polymers: PEG (polyethleneglycol) or PDMS (poly(dimethylsiloxane) layers from methacrylate telechelic monomers of PEG and PDMS . . . ;

(v) the process allows for the versatile production of polymer stemming from ring opening type of polymerization of cyclic monomers such as lactic acid, glycolic acid, ε-caprolactone . . . ;

(vi) the process performs the actual grafting of the polymer layer on the surface, as is illustrated by the fact that a poly-HEMA layer obtained according to the present invention is fully swollen by water and is thus not merely crosslinked and insoluble on the surface: Electrochemical impedance Spectroscopy (EIS) measurements show that the electrochemical impedance of a TiN surface in a NaCl medium is very little modified by a 100 nm poly-HEMA layer obtained by electro-grafting, which shows that ionic current through the film is still active, and that the polymer layer is permeable and does not constitute an insoluble barrier layer to water;

(vii) the process allows for the formation of thin grafted polymer layers which can be used as adhesion primers for much thicker layers sprayed over them: this is illustrated with a 150 nm poly-BUMA layer electro-grafted on a 316L stainless steel coupon, which eliminates delamination of a 5 µm PLA layer sprayed over it when the coupon is pulled apart . . .

(viii) the process allows for the formation of grafted layers essentially composed of the sought polymer. Contrary to the expectations, the electro-reduction of the diazonium and growth on the nitrophenylenes on themselves does not predominate over the initiation of polymerization reactions of the monomer.

Figure 1:
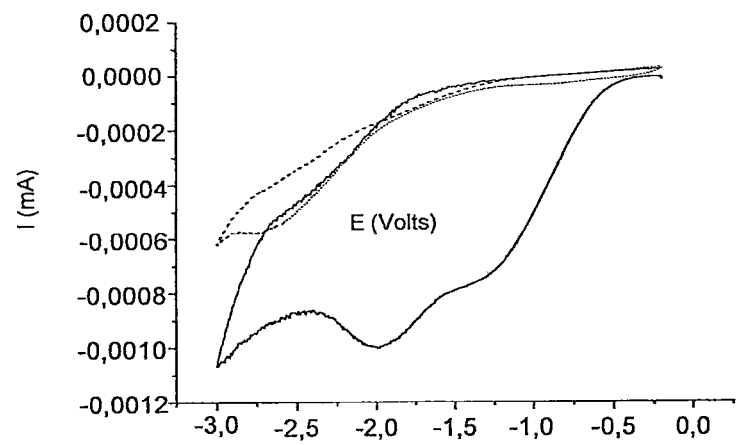
FIG. 1: first (black line) and last (dotted line) cyclic voltammogram of the solution; demonstrating thin film formation.

According to this process, the monomers eligible for the present invention are preferably selected among the activated vinyl monomers and the cyclic molecules cleavable by nucleophilic attack having respectively the formulas (I) and (II):

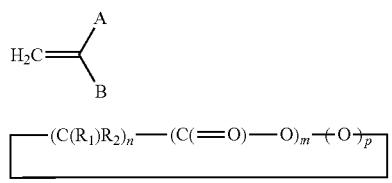

in which:
A, B, $R_1$ and $R_2$, identical or different, represent a hydrogen atom; a C1-C4alkyl group; a nitrile group; a selected organic function among the functions hydroxyl, amine: —NHx with x=1 or 2, ammonium, thiol, carboxylic acids and their salts, ester, amide: C(═O)NHy in which y=1 or 2, imide, imido-ester, acid halide: C(═O)X in which X represents an halogen atom chosen among fluorine, chlorine, bromine and iodine, acid anhydride: —C(═O)OC(═O), amino-acids, phosphonic acids and their salts, phosphoric acids and their salts, phosphonyl choline and its derivatives, sulfonic acids and their salts, sulfuric acids and their salts, nitrile, succinimide, phthalimide, isocyanate, epoxy, siloxane: —Si(OH)z in which z is a whole number ranging between 1 and 3 inclusively, benzoquinone, carbonyl-diimidazole, pare-toluene sulphonyl, para-nitrophenyl chloroformate, ethylene and vinyl, aromatic and in particular toluene, benzene, halogeno-benzene, pyridine, pyrimidin, styrene or halogeno-styrene and their substituted equivalents; a functional group being able to complex cations and in particular reducible cations of metals such as, for example, copper, iron and nickel; molecular structures substituted and/or functionalized starting from these functional groups; thermally or photochemically cleavable groups like diazonium salts, peroxides, nitrenes, azides, nitroso anilides, alkoxyamines and in particular 2,2,6,6-tetramethyl-1-piperidinyloxy (TEMPO), benzophenone and its derivatives, dithioesters, dithiocarbamates, trithiocarbonates; electroactive groups and in particular conducting polymer precursors like aniline, thiophene, methylthiophene, big thiophene, pyrrole, ethylene dioxothiophene (EDOT) and analogues as well as electro-cleavable groups like diazonium, sulfonium, phosphonium and iodonium salts, as well as mixtures of monomers containing the aforementioned groups;

the straight line of formula (II) represents an C3-C10 alkyl radical;

n, m and p, identical or different, are whole numbers ranging between 0 and 20 inclusively, under the proviso that n, m and p are not at the same time 0.

Other cyclic molecules cleavable by nucleophilic attack may also be used. For example, the monomer can be a cyclic compound containing an amine and/or an amide, such as a lactame.

In the notation above, $R_1$ and $R_2$ are groups which depend implicitly on an index i not indicated, i lying between 0 and n. This expresses the fact that the $R_1$ and $R_2$ groups can be in fact different one ($C(R_1)R_2$) from the other in the structure of the cyclic molecules of formula (II), i.e. the notation $(C(R_1)R_2)n$ does not refer to the repetition of the same motif $(C(R_1)R_2)$, but to the succession of $(C(R_1)R_2)$ type groups, where $R_1$ and $R_2$ are included in the list above.

Among the functional groups of the activated vinyl monomers of formula (I) above being able to complex cations, one can in particular quote amides, ethers, carbonyls, carboxyls and carboxylate, phosphines, phosphines oxides, thioethers, disulphides, ureas, ether-crowns, aza-crowns, thio-crowns, cryptands, sepulcrats, podands, porphyrins, calixarenes, bipyridines and terpyridines, quinolines, orthophenantroline compounds, naphthols, iso-naphthols, thioureas, siderophores, antibiotics, ethyleneglycol and cyclodextrins.

Among the activated vinyl monomers of formula (I) above, one can in particular quote acrylonitrile, methacrylonitrile, methyl ethyl, propyl and butyl methacrylate, hydroxyethyl hydroxypropyl glycidyle methacrylate, acrylamides and in particular amino-ethyl, propyl, butyl, pentyl and hexyl methacrylamides, cyanoacrylates, di-acrylates or di-methacrylates, tri-acrylates or tri-methacrylates, tetra-acrylates or tetra-methacrylates (such as pentaerythritol tetramethacrylate), acrylic and methacrylic acid, styrene and his derivatives, parachlorostyrene, pentafluoro-styrene, N-vinyl pyrrolidone, 2-vinyl pyridine, vinyl acryloyle, méthacryloyle halides, di-vinylbenzene (DVB), and more generally agents reticulating vinyl or based on methacrylate acrylate, and their derivatives.

Among the cleavable cyclic molecules of formula (II) above, one can in particular quote epoxies, lactones and in particular butyrolactones, the ε-caprolactone and his derivatives, lactic acids, the glycolic acid, oxiranes, polyaspartate, like their mixtures and their derivatives.

Another object of the invention is a method for grafting an organic film onto an electrically conductive or semiconductive surface by electro-reduction of a solution, wherein the solution comprises at least one diazonium salt and a cyclic monomer which undergoes polymerization by nucleophilic attack cleavage, of formula (II). The polymer is in particular chosen from the group consisting of lactic acid, glycolic acid and ε-caprolactone.

Another subject of the present invention is a method of attaching macro-objects to an electrically conducting or semiconducting surface by electrografting. For the purpose of the present invention, the term "macro-object" is intended to mean any polymeric or nonpolymeric macrostructure functionalized with at least one group that can be involved in propagation chain reactions, i.e. belonging to the family of vinylic groups or of cleavable cyclic molecules such as listed above. In what follows, such groups will be referred to as "chain polymerizable", by analogy with the chain polymerizable monomers described above.

In this embodiment, an object of the invention is a method for grafting an organic film onto an electrically conductive or semiconductive surface by electro-reduction of a solution, comprising the following steps:

a) preparation of a solution containing at least one diazonium salt and one macro-objects, that are precursors of said organic film, b) electrolyzing said solution in an electrolysis cell using the conducting or semiconducting surface to be coated as working electrode and at least one counterelectrode, so as to result, by application of at least one protocols consisting of an electrical polarization of the surface by applying a variable potential over at least a range of values which are more cathodic that the reduction or peak potential of all diazonium salts in the said solution, in a grafted coating of said organic film on said surface.

It may be, for example, any crosslinked or noncrosslinked polymer functionalized at the end of or along its chain, or else in crosslinking zones, or any totally or partially functionalized macromolecule, or an object of nanometric or micrometric size or greater, the surface of which it has been possible to functionalize with at least one chain polymerizable group capable of undergoing or getting involved in a surface initiated polymerization reaction as per the present invention.

A macro-object according to the present invention may, for example, consist of any crosslinked or noncrosslinked polymer functionalized at the end of or along its chain, or else in crosslinking zones, or any totally or partially functionalized macromolecule, or an object of nanometric or micrometric size or greater, the surface of which it has been possible to functionalize with vinyl groups activated with electro-withdrawing groups, such as, for example, the groups: methacrylate, acrylate, vinyl chloride, acrylonitrile, methacrylonitrile, 4-vinylpyridine, 2-vinylpyridine, N-vinylpyrrolidone, etc., or else with cyclic groups, such as epoxy groups or, more generally, oxiranes or lactones such as ϵ-caprolactone.

The use of these macro-objects makes it possible to obtain electrografted films containing the macrostructural portion. The grafting takes place due to the presence, on the macrostructural portion, of the electrophilic or nucleophilic groups. Since these groups are linked to the macrostructural portion, electrografting of this portion onto the surface is obtained.

The macro-objects which can be used in accordance with the present invention, due to the presence of their chain polymerizable functional group(s), can either serve themselves as a monomer and be electro-grafted like a "standard" monomer. In some cases, the molecular structure which is attached to the chain polymerizable groups can be so large that the chain polymerizable groups are impotent, i.e. they do not have enough mobility to be actually the sole actors of the propagation and attachment of the said macro-object to the surface thanks to the electro-grafting. Then it may be necessary to consider the co-electro-grafting of the macro-object with some smaller monomer—for example an efficient vinylic monomer such as butyl methacrylate or hydroxyethyl methacrylate—to achieve the electro-grafting on the surface, achieve chain propagation and film growth and occasionally propagate through the chain polymerizable group of the macro-objects.

The macro-objects which can be used according to the method in accordance with the invention are preferably chosen from the compounds of formulae below:

A-P

A-P—B $P(A)_n$ $[M(A)]_n$

A-$[M(B)]_n$

A-$[M(B)]_n$—C

A-P-$[M(B)]_n$

A-P-[M(B)]—C in which:

(i) P is a macrostructure chosen from: organic or inorganic oligomers and polymers, polymers obtained by polycondensation of one or more reagents, polysiloxanes, poly(orthoesters), polyphosphates, parylene and substituted parylene-based polymers, conducting polymers, oligopeptides and proteins, nucleic acid molecules, polysaccharides, substituted or unsubstituted porphyrins, substituted or unsubstituted phthalocyanins, polymers formed from substituted monomers or from substituted macromolecules from the list above, prepolymers, macromers or telechelics based on the monomers and/or macromolecules from the list above, copolymers and/or mixtures which can be formed from these polymers, from their constituent monomers or from the macromolecules above, which may or may not be substituted; macrostructures which are not polymeric and not strictly macromolecular, such as, for example, those obtained by crosslinking of a two- or three-dimensional network, for instance rubber, etc., mineral aggregates, lipid vesicles such as liposomes and niosomes, and living cells, objects comprising at least one surface which can be functionalized with at least one electroactive group, and in particular an electrograftable group;

(ii) n is an integer greater than or equal to 1;

(iii) M is a constituent monomer unit of the structures of type P defined above when said structures are a polymer;

(iv) A, B and C, which may be identical or different, are chosen from chain polymerizable groups selected from vinylic groups or cleavable cyclic molecules like lactones, lactides, oxiranes, A, B and C being linked via covalent, ionic or dative bonds, or via hydrogen bonding, with the macrostructural portion P or the monomeric portion M.

Among the polymers defined for P, mention may in particular be made of crosslinked or noncrosslinked vinyl polymers, such as, for example, polymers of acrylonitrile, of methacrylonitrile, of methyl methacrylate, of ethyl methacrylate, of propyl methacrylate, of butyl methacrylate, of hydroxyethylmethacrylate, of hydroxylpropylmethacrylate, of cyanoacrylates, of acrylic acid, of methacrylic acid, of styrene and of its derivatives, of N-vinylpyrrolidone, of vinyl halides, and polyacrylamides; polymers of isoprene, of ethylene, of propylene, of ethylene oxide, of molecules containing a cleavable ring, such as lactones, and in particular ϵ-caprolactone, of lactides . . . , of glycolic acid, of ethylene glycol, polyamides, polyurethanes, poly(orthoesters) and polyaspartates.

Among the conducting polymers, mention may in particular be made of those based on aniline, on thiophene or on ethylenedioxythiophene (EDOT), on pyrrole, on their analogs or on their substituted derivatives.

Among the proteins, mention may in particular be made of antigens, enzymes, growth factors, antibodies and collagens.

Among the nucleic acid molecules, mention may in particular be made of single- and double-stranded DNA; and single- and double-stranded RNA.

Among the polysaccharides, mention may in particular, by way of example, be made of cellulose and substituted celluloses, chitosans and substituted or functionalized chitosans, dextrans and substituted or functionalized dextrans, amyloses, pectins, starch and heparin.

Among the mineral aggregates, mention may in particular be made of beads of silica and more generally of oxides, and also nanoobjects of any nature (nanobeads, nanotubes, fullerenes, etc.).

Among the objects having at least one surface which can be functionalized with at least one electroactive group, mention may be made of non-liquid and non-gaseous objects having at least one electrically conducting, semiconducting or insulating surface, chosen from metal, organic or mineral surfaces, such as wood, glass, plastic, plant fibers, keratin materials, organic or mineral gels, composites thereof or mixtures thereof.

The maximum number which can be defined for n is not critical according to the invention and depends on the number of functions present on the macrostructural portion that are capable of being functionalized with chain polymerizable group.

This functionalization may, for example, be carried out by exploiting the reaction of these hydroxyl groups with methacryloyl chloride (MAC) so as to form methacrylic esters, which will introduce a methacrylate—chain polymerizable—group into the macrostructure, and will allow it to be electro-grafted according to the method in accordance with the present invention.

The same type of reactions can, for example, be envisioned with glycidyl methacrylate in place of the methacryloyl chloride.

The use of molecules which can serve as spacer elements, such as diisocyanates, epichlorohydrin and, more generally, any bifunctional molecule, in order to obtain the formation of a covalent bond between a vinyl monomer and a macrostructure, can also be considered. The concentration of the electrophilic macro-object in the electrolyte solution is preferably between $10^{-6}$ and 5 mol/l.

The concentration in chain polymerizable groups or in monomers within the electrolytic solution according to the process in conformity with the invention is variable of a monomer to another. However this concentration preferably lies between 0.1 and 10 mol/l and even more preferentially between 0.1 and 5 mol/l.

The concentration in diazonium salt within the electrolytic solution according to the process in conformity with the invention preferably lies between 1 and $10^{-4}$ mol/l and even more preferentially between $10^{-2}$ and $10^{-3}$ mol/l.

According to a particular embodiment of the process in conformity with the invention, the electrolytic solution can include moreover at least an additional liquid (solvent) primarily spectator (i.e. not intervening in the electropolymerisation reaction) intended to solubilize the chain polymerizable monomers which would not be or not very water soluble in order to enable them to be driven to meet. However, it is important to note that the presence of such a liquid is not always necessary because one can consider situations where the monomers used are used pure, or where some of the monomers of a mixture of monomers are used as solvent, or where all the monomers of a mixture of monomers are in miscible proportions. When they are used, these solvents are preferably selected among the dimethylformamide, the dimethylsulfoxide, the ethyl acetate, the acetonitrile, the tetrahydrofuranne, the propylene carbonate and other solvents usually used in electrochemistry, dichloroethane and more generally chlorinated solvents. The solvent can also be chosen from the group consisting of water and alcohols. The process in conformity with the invention having the advantage of allowing the direct use of these solvents without having to subject them to prior distillation in order to eliminate water which they contain, nor to carry out a rigorous control of the water content of the atmosphere above the reaction medium. So the process in conformity with the invention can easily be implemented on an industrial scale.

In a preferred embodiment of the invention, the electrolytic solution includes dimethylformamide alone or mixed with water or dimethylsulfoxide.

In the same way, according to another embodiment of the process in conformity with the invention, the electrolytic solution can also contain at least a supporting electrolyte in order to ensure and/or to improve the passage of the current in the electrolytic solution. The use of an electrolyte support is however not mandatory, for example if the chain polymerizable monomer used comprises itself ionic groups (as for example the aminohexyl methacrylate ammonium chloride) which then ensure the maintenance of the electric circuit ohmic drop at an acceptable value. When they are used, the supporting electrolytes are preferably selected among quaternary ammonium salts such as perchlorates, tosylates, tetrafluoroborates, hexafluorophosphates, quaternary ammoniums halides, sodium nitrate and sodium chloride. Among these quaternary ammonium salts one can in particular quote by way of example tetraethylammonium perchlorate (TEAP), the tetrabutylammonium perchlorate (TBAP), tetrapropylammonium perchlorate (TPAP), the benzyltrimethylammonium perchlorate (BTMAP).

The electrolytic solution can further comprise an agent for improving the homogeneity of the film (a surfactant), such as glycerol.

According to the invention, the electrically conductive or semiconductive surface is preferably a surface of stainless steel, cobalt and its alloys (for example Co—Cr—Mo, Co—Cr—W), titanium and its alloys (for example Nitinol, NiTi) materials being particularly preferred according to the invention in the biomed, iron, copper, nickel, niobium, aluminum (in particular when it is freshly brushed), of silver, silicon (doped or not), silicon carbide, titanium nitride, tungsten, nitride of tungsten, tantalum, nitride of tantalum or a noble metal surface chosen by platino-iridium or iridium, platinum, gold surfaces.

In the process according to the invention, the electrolysis of the electrolytic solution can be carried out by polarization of the surface to be coated under voltammetric conditions, as well as via any potential- or current-controlled protocol in which the potential (rasp. the current) is time dependent. The present invention also relies on the fact that when one applies a time-dependent electrode potential protocol, provided that this protocol contains cathodic excursions at potentials which are higher than a certain threshold, with an electrode dipped in an electrolytic bath comprising at least a diazonium salt and at least a molecule bearing at least one chain polymerizable group, then one can obtain—after rinsing—the formation of a polymeric film containing the said group. The threshold under consideration in the present invention is at least the reduction potential of the diazonium in the solution: it is necessary that over at least a part of the potential (or current) protocol applied to the substrate, the potential of the surface be higher than that of the highest diazonium salt present in the solution In a preferred embodiment, the threshold under consideration in the present invention is at least the reduction potential of the aryl diazonium in the solution: it is necessary that over at least a part of the potential (or current) protocol applied to the substrate, the potential of the surface be higher than that of the highest aryl diazonium salt present in the solution. Without willing to be bound by theory, it is thought that this enables the actual grafting of the aryl group onto the surface, and the subsequent attachment of the polymer to the surface via said aryl groups thanks to a radical aromatic substitution. In such a scheme, the polymer would be formed thanks to either some non grafted or chemisorbed aryl radicals which would act as initiators, or some other radicals stemming e.g. from the reduction of protons and/or from the solvent itself. Preferred experimental conditions include, for example, performing polarization under voltammetric conditions from the resting potential of the substrate in the solution Referring to example 15, one notes that the best polymeric films (essentially composed of the polymer, with low content in diazonium) are obtained for an excursion in cathodic at about the potential range for the reduction of the monomer.

These results demonstrate that best polymer films are obtained at potentials which are greater than those of the reduction of the diazonium salts, and that eventhough the diazonium salts are key in obtaining an operational process for the electro-grafting of polymer layers, the best working potentials are much more cathodic, close to those of the reduction of the substituent group of the diazonium and/or of the monomer itself.

According to a preferred embodiment, the applied potential has excursions in potential ranges which are the most cathodic potential accessible within the solvent window before the so-called "solvent wall". This solvent wall is usually identified very easily in the voltammograms, as it corresponds to the potential at which a very steep rise (in absolute value) of the electrochemical current is observed, well above the maximum of the current peak stemming from the electro-reduction of the diazonium salt. The nature of the electrochemical reactions accompanying this steep increase in the cathodic current may vary in proportions from one electrochemical medium to another, but usually correspond to the reduction of either the supporting electrolyte, or the solvent, or dissolved water (in the case when water Is not the solvent), or all of these together. Typically, according to this embodiment, applied potentials in the invention may have excursions up to −2 to −3 V/ECS i.e. 1 to more than 2 V more cathodic than the reduction peak of the diazonium.

When the solvent is water or contains water, the skilled person knows that the applied potential must be lower than the proton reduction potential.

The choice of the potential value may be a critical feature of the process (see examples 12 and 13).

In a preferred embodiment of the invention, the film is obtained by successive application of several protocols selected independently from protocols with variable applied working potential and protocols with variable applied working current, each protocol being applied to the surface for a given duration that is identical to or different from that of the other protocols.

The invention, in addition, aims also at producing electrically conductive or semiconductive areas of a surface coated with an electro-grafted film as described above. In general, these coatings have a thickness between 10 nm and 10 μm, and preferably between 10 nm and 1 μm.

The diazonium salt is a diazonium salt or a mixture of diazonium salts of generic formula R'—$N^{2+}$, $X^-$, in which R' contains one or more aromatic ring(s) and/or one or more unsaturated group(s), and $X^-$ is a counterion.

R' preferably comprises an organic or mineral group selected from the group consisting of: nitro, fluoro, bromo, choro, iodo, thiocyanato, sulphate, sulphonate, sulphonium salts, phosphate, phosphonate, phosphonium salts, diazonium salts, amine, ammonium, alcohol, aldehyde, ketone, carboxylic acid, ester, amide, nitrile, anhydride, acid halide, alkyl, alkenyl, alkynyl, aryl, naphthyl, anthryl, pyrryl and polyaromatic groups of higher degree, and wherein the alkyl, alkenyl, alkynyl, aryl, naphthyl, anthryl, pyrryl and polyaromatic groups of higher degree include a group selected from the group consisting of: nitro, fluoro, bromo, chloro, iodo, thiocyanato, sulphate, sulphonate, sulphonium salts, phosphate, phosphonate, phosphonium salts, diazonium salts, amine, ammonium, alcohol, aldehyde, ketone, carboxylic acid, ester, amide, nitrile, anhydride, and acid halide.

According to a preferred mode of achievement, the process of the invention is characterized in that the diazonium salt is an aryl diazonium salt, preferably of formula $ArN_2^+$ $X^-$, in which Ar represents an aromatic group and X represents an anion advantageously selected among: halogens, sulphates, phosphates, perchlorates, tetrafluoroborates, hexafluorophosphates and carboxylates.

The anion can be a substituent of the aryl group for example a sulphonate group, one obtains an amphiphilic molecule then comprising a diazonium salt.

The aromatic group can contain one or more aromatic groups linked together or fused. It can be a C6-C14 aromatic moiety, possibly substituted by one or more functional substituents or a heteroaromatic moiety having from 4 to 14 atoms, possibly substituted by one or more functional substituents, comprising one or more heteroatoms selected among oxygen, nitrogen, sulphur or phosphorus. The aromatic group may furthermore comprise one or more substituents chosen from the group consisting of:

aliphatic radicals, linear or ramified from 1 to 20 carbon atoms, possibly comprising one or more double or triple bond, possibly substituted by carboxyl radicals, $NO_2$, protected disubstituted and monosubstituted amino groups, cyano, diazonium, alkoxy containing from 1 to 20 carbon atoms, alkoxycarbonyle containing from 1 to 20 carbon atoms, alkylcarbonyloxy containing from 1 to 20 carbon atoms, possibly fluorinated vinyl or allyl, the halogen atoms radicals aryls possibly substituted by radicals carboxyls, $NO_2$, cyano, diazonium, alkoxy containing from 1 to 20 carbon atoms, alkoxycarbonyle containing from 1 to 20 carbon atoms, alkylcarbonyloxy containing from 1 to 20 carbon atoms, possibly fluorinated vinyl or allyl, the halogen atoms radicals carboxyls, $NO_2$, protected disubstituted, monosubstituted amino groups amido, cyano, diazonium, sulphonic, phosphonic, alkoxy containing from 1 to 20 carbon atoms, alkoxycarbonyle containing from 1 to 20 carbon atoms, alkylcarbonyloxy containing from 1 to 20 carbon atoms, possibly fluorinated vinyl, the halogen atoms.

According to a preferred mode of achievement, the process of the invention is characterized in that the aromatic group comprises one or more substituents likely to react directly with organic resins, biological molecules, chemical molecules or complexing agents, or one or more precursory substituents which, after transformation, are likely to react with organic resins, biological molecules, chemical molecules or sequestering agents. The expression "substituents likely to react directly with polymers, chemical or biological molecules" indicates the substituents of the aromatic group fixed on the surface and having reactive functions likely to react with the chemical functions carried by other molecules. The examples of reactive functions carried by the aromatic group are the allyl or vinyl or acetylenic functions, the halogens, alcohols, for example of type —$(CH_2)n$-$CH_2$—OH, the carboxylic acids, for example of type —$(CN)n$-COOH, the anhydrides or halides of acid, the nitriles, the isocyanates, the amines, for example of type —$(CH_2)n$-$NH_2$, n being a whole number varying from 0 to 10, sulphonic acids or sulphonates, phosphonic acids or phosphonates. The expression "precursor substituents which, after transformation, are likely to react with polymers, chemical or biological molecules" indicates substituents which after one or more transformations are likely to react with polymers, chemical or biological molecules. The precursory substituents which, after transformation, are likely to react are, for example, $NO_2$, $N^{2+}$, $(CH)_n$—CN, $(CH_2)_n$—CHO, $(CH_2)_n$—COOPr, Pr being a protective group, —$(CH_2)_n$—NHP'R, $(CH_2)_n$—N(P'r)$_2$, $(CH_2)_n$—N=P''R, P'R, P''R being protective groups, n being a whole number varying from 1 to 10. The phenacyl sulphonyl chloride or the acetyl chloride is examples of amines protective groups.

The process can comprise a further step of applying an outer coating. This outer coating can be applied by electro-deposition or by another means like dip coating, spray coating or spin coating.

A further object is an electrically conductive or semiconductive surface having an organic film grafted thereto obtained by the process according to the invention Thanks to the process of the invention, thick coatings of organic film can be obtained. It can be observed in the following examples that organic films of 300 nm can be obtained (see, for instance, examples 1 and 9). Example 3 shows that when a cross-linking agent is used, thicker films can be obtained. The grafted film has preferably a thickness of between 1 nm and 10 μm, more preferably of between 10 nm and 1 μm.

The surface is an electrically conductive and semiconductive surface. The surface can be in particular stainless steel, steel or a cobalt-chromium alloy. Therefore, the present process allows the coating with an organic film (in particular vinylic polymer) of all conductive and semiconductive surfaces.

The organic film can be a vinylic polymer or copolymer, in particular poly-BUMA, poly-HEMA, poly-MPC/BUMA and poly-MPC/DMA/TMSPMA. In a preferred embodiment, the organic film is a biodegradable polymer, in particular a polycaprolactone or a PLA.

It can be observed in the following examples that the organic film comprises the chemical structure of the monomer (either one monomer or various monomers) and a moiety of the diazonium salt (when an aryl diazonium salt is used, the aryl moiety is present in the organic film—see for instance example 1)

As shown in example 16, the electro-grafted polymeric film is not homogeneous in a direction perpendicular to the surface: close to the metallic surface, the film is richer in diazonium and its electro-reduction by-products, while farther from the surface, the film is richer in polymer. This "dual" structure of the film is an interesting result as: (i) diazonium salts are more easily graftable on conducting or semi-conducting surfaces than monomers. In the case of vinylic monomers, it is believed that this is because vinylics are reduced to radical anions which are primarily repelled by the (negatively) polarized surface as they are formed, during their electro-reduction: hence, the electro-grafting of vinylics is a phenomenon with very low yield with respect to the current. Practically, the electro-grafting of monomers, notably vinylics, is difficult on common surfaces, especially when residual oxide layers are present. Still from a practical standpoint, diazonium salts are more readily electro-grafted, with great compliance, on usual surfaces. The present invention thus transfers to monomers, notably vinylics, the compliance observed with the diazonium salts. Moreover, the electro-grafting of diazonium salts is little sensitive to water content, a feature which is observed in the present invention, while the direct electro-grafting of monomers, notably vinylics, is very sensitive to water content; (ii) the layers obtained via the electro-grafting of diazonium salts are more dense than those obtained with monomers (vinylics), and afford an excellent covalent link even with thin oxide layers as soon as they are at least semi-conductive, thus affording a good electro-grafting and adhesion of a polymer in conditions in which the direct electro-grafting of monomers (vinylics) would fail.

The organic film obtained by the present process:
can be a biocompatible film;
can be an adhesion primer;
can have electrical conduction properties;
can have electrically insulating properties.

A further object of the invention is an electrolytic composition comprising at least one diazonium salt, one monomer bearing at least one chain polymerizable functional group and one supporting electrolyte. The diazonium salt, the monomer and the supporting electrolyte have the same definition as above. In a particular embodiment, the monomer is chosen from the group consisting of butylmethacrylate, hydroxyethylmethacrylate, lactic acid, glycolic acid and ε-caprolactone. The composition advantageously further comprises a solvent (as defined above) and/or a surfactant (glycerol). The electrolytic composition advantageously comprises the monomer at a concentration of 1.5 to 2 mol/l, the diazonium salt at a concentration of $5.10^{-4}$ to $10^{-1}$ mol/l, the supporting electrolyte at a concentration of $10^{-3}$ to $5.10^{-2}$ mol/l.

The invention is also directed to an electrolytic composition comprising
a monomer chosen from the group consisting of butyl-methacrylate and hydroxyethylmethacrylate,
at least one diazonium salt,
a supporting electrolyte, and
a solvent The electrolytic composition advantageously comprises the monomer at a concentration of 1.5 to 2 mol/l, the diazonium salt at a concentration of $5.10^{-4}$ to $10^{-1}$ mol/l, the supporting electrolyte at a concentration of $10^{-3}$ to $5.10^{-2}$ mol/l.

In particular, the diazonium salt is an aryl diazonium salt. The supporting electrolyte is advantageously chosen from the group consisting of $NaNO_3$ and TEAP. For these polymers, the use of a solvent, especially DMF, may be recommended.

A further object of the invention is an electrolytic composition comprising
butylmethacrylate monomer, at a concentration of 1.5 to 2 mol/l
glycerol, at a concentration of 0.01 to 1 mol/l
Dimethyl Formamide as the solvent,
4-nitrophenyl diazonium tetrafluoroborate at a concentration of $5.10^{-4}$ to $10^{-1}$ mol/l
sodium nitrate (NaNO3) at a concentration of $10^{-3}$ to $5.10^{-2}$ mol/l.

The invention also relates to a method for preparing a formulation for electrografting comprising the following successive steps
a) preparation of a composition comprising
butylmethacrylate monomer, at a concentration of 1.5 to 2 mol/l
glycerol (5% of the total volume), at a concentration of 0.01 to 1 mol/l
Dimethyl Formamide as the solvent,
sodium nitrate (NaNO3) at a concentration of $10^{-3}$ to $5.10^{-2}$ mol/l.
b) addition to said composition, prior to use, 4-nitrophenyl diazonium tetrafluoroborate, at a concentration of $5.10^{-4}$ to $10^{-1}$ mol/l.

A further object of the invention is an electrolytic composition comprising
- hydroxyethylmethacrylate monomer, at a concentration of 1.5 to 2 mol/l
- glycerol; at a concentration of 0.01 to 1 mol/l
- Dimethyl Formamide as the solvent,
- 4-nitrophenyl diazonium tetrafluoroborate at a concentration of $5.10^{-4}$ to $10^{-1}$ mol/l
- sodium nitrate (NaNO3) at a concentration of $10^{-3}$ to $5.10^{-2}$ mol/l.

The invention also relates to a method for preparing a formulation for electrografting comprising the following successive steps
a) preparation of a composition comprising
- hydroxyethylmethacrylate monomer, at a concentration of 1.5 to 2 mol/l
- glycerol, at a concentration of 0.01 to 1 mol/l
- Dimethyl Formamide as the solvent,
- sodium nitrate (NaNO3) at a concentration of $10^{-3}$ to $5.10^{-2}$ mol/l.

b) addition to said composition, prior to use, 4-nitrophenyl diazonium tetrafluoroborate, at a concentration of $5.10^{-4}$ to $10^{-1}$ mol/l.

The invention further relates to a process of coating a stent with an electro-grafted layer of poly-Hydroxyethylmethacrylate comprising the following steps:
- Cleaning with Detergent with Ultra-sonic 35 kHz power 90% for 1.0 to 20 min;
- Rinsing with DI Water with Ultra-sonic 35 kHz power 90% for 10 to 90 min;
- Drying;
- Contacting the stent with cathode of a power supply;
- Dipping in electrolytic solution of claim 25 with argon bubbling for 5 to 20 min;
- Polarizing stent via a cyclic voltammetry protocol, scanning between 5 and 75 times from open circuit potential to −3 V/CE (CE=counterelectrode=the anode) at a scanning rate of 100 mV/s, with argon bubbling at 8 l/min;
- First rinsing in DMF with argon bubbling for 5 to 20 min;
- Second rinsing in with argon bubbling DMF for 5 to 20 min;
- Rinsing in DI Water for 5 to 20 min;
- Drying in Vacuum oven at 40° C., 10 mbars for 30 to 180 min.

The invention further relates to a process of coating a stent with an electro-grafted layer of poly-Butylmethacrylate comprising the following steps:
- Cleaning with Detergent with Ultra-sonic 35 kHz power 90% for 10 to 20 min;
- Rinsing with DI Water with Ultra-sonic 35 kHz power 90% for 10 to 90 min;
- Drying;
- Contacting the stent with cathode of a power supply;
- Dipping in electrolytic solution of claim 23 with argon bubbling for 5 to 20 min;
- Polarizing stent via a cyclic voltammetry protocol, scanning between 5 and 75 times from open circuit potential to −3.2 V/CE (CE=counterelectrode=the anode) at a scanning rate of 50 mV/s, with argon bubbling at 8/min;
- First rinsing in DMF with argon bubbling for 5 to 20 min;
- Second rinsing in with argon bubbling DMF for 5 to 20 min;
- Rinsing in DI Water for 5 to 20 min;
- Drying in Vacuum oven at 40° C., 10 mbars for 30 to 180 min.

EXPERIMENTAL

All chemicals were obtained from Aldrich Chemical Company or Acros, and were used as received. TiN thin films were obtained by MOCVD on $SiO_2$/Si substrates.

The typical coupon size was 7×1 $cm^2$. The electropolished stainless steel (316L), cobalt chromium (MP35N) sand blasted and non sand blasted titanium substrates were cleaned for 30 minutes under ultrasounds at 50° C. in a solution of Dorex 2% then in distilled water and dried 1 hour in an oven at 100° C. before use. The TiN/$SiO_2$/Si substrates that were used as received from the MOCVD deposition chamber.

A Brucker Tensor 27 Fourier transform infrared spectrometer (FT-IR) provided with a SensIR (Durascope) accessory for ATR measurements was used to characterize the composition of the coating at a resolution of 4 $cm^{-1}$. The thickness films were measured by carving a sharp furrow through the film with a cutter and measuring the depth of this furrow with a Step IQ profilometer from KLA Tencor. The voltammetric and other time dependent potential experiments were performed with a potentiostat/galvanostat (CH660 A, CH Instruments, USA), in which the potential of the working electrode (the substrate to be coated) is imposed with respect to a calomel reference electrode (ECS). Unless otherwise specified, all potentials are implicitly indicated with respect to the ECS reference potential in all experiments. The XPS spectra were obtained on a ESCALAB VG XL 220 equipment (source: Al, energy: 1486.6 eV). ToF-SIMS spectra were obtained on a ToF-SIMS IV (ION-TOF GmbH, Münster, Germany). The acquisition time was 75 s and the spectra were acquired over an area of 150×150 $nm^2$. Spectra were obtained with the Au source (25 keV) operated in a high mass resolution mode. Both the positive and the negative spectra were recorded.

The electrochemical impedance spectroscopy experiments were performed using a three electrodes electrochemical cell, with a large platinum foil as counter electrode and a Ag/AgCl reference electrode. The EIS spectra were collected using a multichannel potentiostat VMPII/z which are controlled by a computer with EcLab software. The measurements were performed at the open circuit potential in the NaCl 0.9 g·$L^{-1}$ solution over a frequency range from $10^5$ to $10^{-2}$ Hz with 5 measured frequencies per decade and 10 mV peak to peak sine wave amplitude signal.

The present invention will hereinafter be described more specifically by the following Examples. It should, however, be borne in mind that the present invention is by no means limited to the following Examples.

Example 1: Deposition of BUMA Thin Films on Stainless Steel in the Presence of 4-Nitrodiazonium Tetrafluoroborate Poly-BUMA films are known to be biocompatible coatings which are important to be deposited as films on biocompatible substrates used for prostheses such as stainless steel, titanium (example 4), CoCr (example 5). Such films are obtained as follows: in 50 mL of undistilled DMF (dimethylformamide), containing 574 mg of TEAP (tetraethylammoniumperchlorate, 2.5 $10^{-2}$ M as a supporting electrolyte) one introduces 50 mL of butylmethacrylate (3.5M) and 236 mg of 4-nitrobenzenediazonium tetrafluoroborate ($10^{-2}$M). This solution is introduced in a two electrodes cell, the working electrode being a coupon of polished stainless steel and the counter electrode a piece of carbon paper. The potential of the stainless steel cathode is scanned 20 times from −0.2 V to −3.0 V at a rate of 100 mV/s with Argon bubbling (2 Lmin$^{-1}$).

In FIG. 1, the first (black line) and last (dotted line) cyclic voltammogram of the solution are reported, demonstrating thin film formation.

On the electrode which is then carefully rinsed DMF, water and air dried is present a 300 nm thick, homogeneous, greenish film. In the IR spectrum of the film, the carbonyl vibration of the polybutylmethacrylate is observed at 1728 cm$^{-1}$ and the two symmetric and antisymmetric vibrations of the nitrophenyl group at 1520 and 1350 cm$^{-1}$, respectively.

One shall notice that a poly-BUMA layer is obtained even though poly-BUMA is readily soluble in DMF. Moreover, this film withstands thorough rinsing in DMF even under ultrasounds for 2 minutes.

Example 2: Deposition of Poly-BUMA Thin Films on Stainless Steel in the Presence of 4-Nitrodiazonium Tetrafluoroborate with Pulse Train Potential Scanning potentials can be used as for example 1 or pulse train potential as it is described in the following experimental procedure.

The same procedure as that given in example 1 was employed except than the pulse train potential ($E_i$=−0.5V during 0.6 s and $E_f$=−3.0 V during 0.3 s) have been used in place of the scanning potential. The scan number was 2000. On the electrode which is then carefully rinsed DMF, water and air dried is present a 300 nm thick, homogeneous, greenish film.

In the IR spectrum of the film, the carbonyl vibration of the polybutylmethacrylate is observed at 1728 cm$^{-1}$ and the two symmetric and antisymmetric vibrations of the nitrophenyl group at 1520 and 1350 cm$^{-1}$, respectively.

Example 3: Cross Linking Agent (Pentaerythritol Tetraacrylate) Effect on the Film Thickness Obtained from Methylmethacrylate and 4-Nitrobenzenediazonium Tetrafluoroborate on Stainless Steel Typically, the thicknesses of films obtained by the vinylic/diazo copolymerisation are about several hundreds of nm. One can obtain thicker films by adding cross linking agent such as pentaerythritol tetraacrylate in the film deposition bath as described in the following procedure.

In 50 mL of undistilled DMF, containing 210 mg of NaNO$_3$ (2.5 10$^{-2}$ M as a supporting electrolyte) one introduces 50 mL of methylmethacrylate (5M), 236 mg of 4-nitrobenzenediazonium tetrafluoroborate (10$^{-2}$M) and with or without 1 mL of pentaerythritol tetraacrylate (1.2 10$^{-3}$M). This solution is introduced in a two electrodes cell, the working electrode being a coupon of polished stainless steel and the counter electrode a piece of carbon paper.

The potential of the stainless steel cathode is scanned 100 times from −0.17 V to −2.8 V at a rate of 50 mV/s with Argon bubbling (2 Lmin$^{-1}$).

On the electrode which is then carefully rinsed DMF, water and air dried is present a homogeneous, greenish film. With pentaerythritol, the film thickness is 1.0 μm. Without pentaerythrol tetraacrylate, it is limited to 150 nm.

Figure 2:
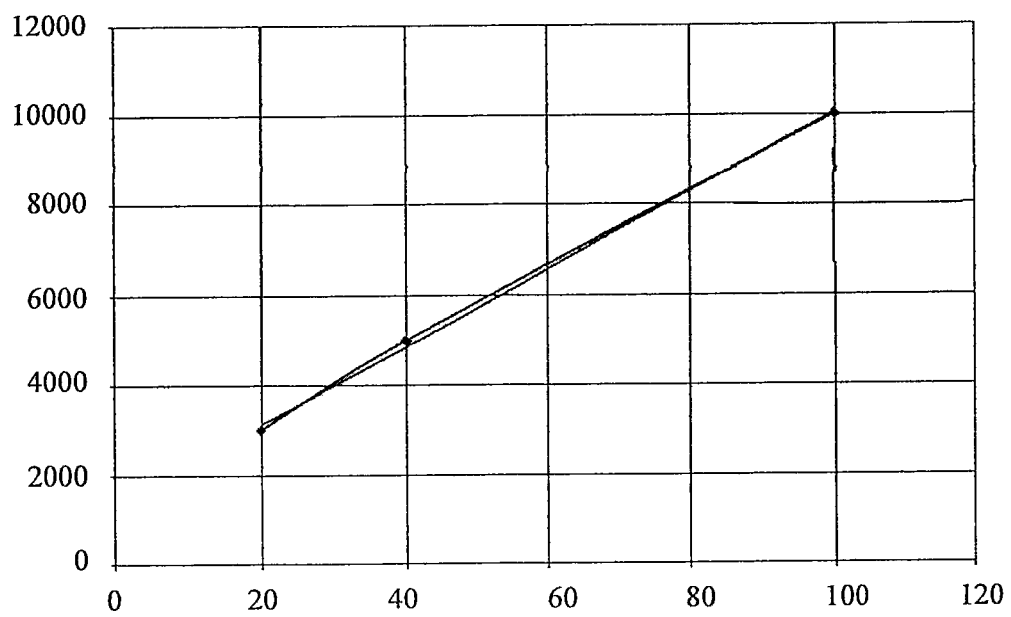
FIG. 2: thickness evolution of films obtained from MMA and 4-nitrobenzenediazonium tetrafluoroborate in the presence of pentaerythritol tetraacrylate on stainless steel coupons according to the number of electrochemical cycles. Abscissa: number of cycles; Ordinate: thickness of the film (Å)

In separated experiments with pentaerythritol tetraacrylate in the same conditions but with respectively 20 and 40 potential scans, thinner film thickness were obtained that thickness is linear according to the number of imposed cycles of voltammetry as it is seen in FIG. 2.

FIG. 2: thickness evolution of films obtained from MMA and 4-nitrobenzenediazonium tetrafluoroborate in the presence of pentaerythritol tetraacrylate on stainless steel coupons according to the number of electrochemical cycles. Abscissa: number of cycles; Ordinate: thickness of the film (Å)

In IR spectra, the carbonyl vibration of the polyester is observed at 1740 cm$^{-1}$ and the two symmetric and antisymmetric vibrations of the nitrophenyl group at 1520 and 1350 cm$^{-1}$, respectively.

Example 4: Deposition of Poly-BUMA Thin Films on Sand Blasted and Non Send Blasted Titanium Substrates in the Presence of 4-Nitrobenzenediazonium Tetrafluoroborate The same procedure as that given in example 1 was used except that sand blasted and non sand blasted titanium substrates were used in place of stainless steel.

On the IR spectrum of the 300 nm thick film on bulk Ti, the carbonyl vibration of the polybutylmethacrylate is observed at 1728 cm$^{-1}$ and the two symmetric and antisymmetric vibrations of the nitrophenyl group at 1520 and 1350 cm$^{-1}$, respectively.

In the case of the sand blasted Ti, we note a change of the hydrophilic/hydrophobic character of the surface after treatment: a water drop contact angle increases from near 0° before treatment to almost 90° after film deposition, stemming from the very hydrophobic poly-BUMA film obtained by electro-grafting.

Example 5: Deposition of Poly-BUMA Thin Films on CoCr (MP35N) Substrates in the Presence of 4-Nitrobenzenediazonium Tetrafluoroborate In 50 mL of undistilled DMF, containing 215 mg of NaNO$_3$ (2.5 10$^{-2}$M as a supporting electrolyte) one introduces 50 mL of butylmethacrylate (3.5M) and 236 mg of 4-nitrobenzenediazonium tetrafluoroborate (10$^{-2}$M). This solution is introduced in a two electrodes cell, the working electrode being a coupon of the electropolished CoCr substrate (MP35N) and the counter electrode a piece of carbon paper. The potential of the stainless steel cathode is scanned 20 times from −0.3 V to −3.5 V at a rate of 100 mV/s with Argon bubbling (2 Lmin$^{-1}$).

On the electrode which is then carefully rinsed DMF, water and air dried is present a 300 nm thick, homogeneous, greenish film. In the IR spectrum of the film, the carbonyl vibration of the polybutylmethacrylate is observed at 1728 cm$^{-1}$.

Example 6: Deposition of Poly-BUMA Thin Films on CoCr (L605) Substrates in the Presence of 4-Nitrobenzenediazonium Tetrafluoroborate The same device setup as that of example 5 is used, except that substrate is a 18 mm L605 cobalt-chromium coronary stent. The composition of the electrolytic solution is the following: butylmethacrylate (30% by weight), 4-nitrobenzenediazonium tetrafluoroborate (10$^{-3}$ M), NaNO$_3$ (2.5.10$^{-2}$ M), Glycerol (5% by weight), DMF (65% by weight); percentages by weight in reference with the total weight of the composition.

After electro-grafting, the stent is rinsed in DMF and dried for 60 minutes at 40° C. under a 10 mbar vacuum. Before the electrografting, stent surface is treated by a solution of NH$_4$F 40% for 1 minute. Using that method the obtained coating thickness is about 150 nm. Electrografting parameters: Cyclic voltammetry from open-circuit potential to −3.5V/CE with argon bubbling (2 l·min⁻¹). Scan number: 50 scans. Scanning rate: 50 mV/s. TOF-SIMS analysis on the stent shows the peaks characteristic of p-BUMA. The same spectra also evidence the absence of peaks characteristic of glycerol.

Example 7: Deposition of Poly-HEMA Thin Films on Stainless Steel in the Presence of 4-Nitrobenzenediazonium Tetrafluoroborate Poly-HEMA is another example of a biocompatible polymer. While poly-BUMA is considered as hydrophobic, poly-HEMA with its hydroxyl group is seen as a more hydrophilic polymer. A poly-HEMA films can be obtained on stainless steel, TiN thin film (example 7), Nitinol (example 8) in the following conditions.

In a mixture of 10 mL of undistilled DMF and 66 mL of desionized water, containing 145 mg of NaCl ($2.5.10^{-2}$M as a supporting electrolyte) one introduces 24 mL of hydroxyethylmethacrylate (HEMA, 2 M) and 236 mg of 4-nitrobenzenediazonium tetrafluoroborate ($10^{-2}$M). This solution is introduced in a three electrodes cell, the working electrode being a coupon of polished stainless steel, the counter electrode a piece of carbon paper end the reference an Ag/AgCl electrode. The potential of the stainless steel cathode is scanned 100 times from −0.1 V to −1.2 V at a rate of 100 mV/s with Argon bubbling (2 Lmin⁻¹).

In the IR spectrum of the film, the carbonyl and the C—OH vibrations of the polyhydroxyethylmethacrylate are observed at 1728 and 1164 cm⁻¹ respectively. The two vibrations of the nitrophenyl group are hardly detectable.

Example 8: Deposition of Poly-HEMA Thin Films on TiN in the Presence of 4-Nitrobenzenediazonium Tetrafluoroborate The same procedure as that given in example 7 was employed except that TiN/SiO₂/Si substrates were used in place of polish stainless steel. The FT-IR of the obtained film shows the carbonyl and the C—OH vibrations of the polyhydroxyethylmethacrylate at 1704 and 1152 cm⁻¹ respectively.

Example 9: Deposition of Poly-HEMA Thin Films on NiTi (Nitinol) in the Presence of 4-Nitrobenzenediazonium Tetrafluoroborate In a mixture of 240 mL of deionized water, containing 58.5 mg of NaCl (0.1 M as a supporting electrolyte) one introduces 60 mL of hydroxyethylmethacrylate (HEMA, 20% in volume) and 144 mg of 4-nitrobenzenediazonium tetrafluoroborate ($10^{-2}$M). This solution is introduced in a two electrodes cell, the working electrode being a coupon of Nitinol, the counter electrode a piece of carbon paper. The potential of the Nitinol cathode is scanned 100 times from −0.7V to −2.5V at a rate of 100 mV/s with Argon bubbling (2 Lmin⁻¹).

In the IR spectrum of the film, the carbonyl and the C—OH vibrations of the polyhydroxyethylmethacrylate are observed at 1728 and 1164 cm⁻¹ respectively. The two vibrations of the nitrophenyl group are hardly detectable. The surface of the electro-grafted substrate is hydrophillic, as seen pe water droplet shape.

Example 10: Deposition of Poly-MPC/BUMA Copolymer Thin Films on Stainless Steel in the Presence of 4-Nitrobenzenediazonium Tetrafluoroborate We have evaluated the mixing of monomers in the solution composition with variable quantity of 2-methacryloyloxyethyl-2-trimethylammoniummethylphosphate (or 2-methacryloyloxyethyl phosphorylcholine, MPC):

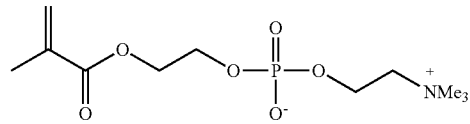

This monomer was synthetized as described in Ishihara K, Ueda T, Nakabayashi N. *Polym J* 1990; 22: 355-360.

This composition is based on a mixture of 210 mL of undistilled DMF, containing 640 mg of NaNO₃ with a constant volume of butylmethacrylate (BUMA) approximately 30% and with an increasing amount of MPC (see table 9-1) and 72 mg of 4-nitrobenzenediazonium tetrafluoroborate ($10^{-2}$M). The volume solution was maintained at 300 mL. This solution is introduced in a two electrodes cell, the working electrode being a coupon of polished stainless steel, the counter electrode a piece of carbon paper. The potential of the stainless steel cathode is scanned 50 times from −0.5 V to −3.2 V at a rate of 50 mV/s with Argon bubbling (2 Lmin⁻¹).

TABLE 1 comparison between the starting electrografting composition solution and the MPC/BUMA ratio into the obtained film on stainless steel substrates

| Sample n° | Starting solution | Results | Technique used & MPC/BUMA ratio |
|---|---|---|---|
| 1 | MPC = 5 g | Blue, 250-300 nm | TOF SIMS: 60% |
| 2 | MPC = 4 g | Blue, 350-400 nm very homogenous | XPS: 51% IR: 42% |
| 3 | MPC = 0.8 g | Blue, 350-400 nm very homogenous | XPS: 6% IR: 3% |
| 4 | MPC = 0.3 g | Blue, 350-400 nm | XPS: 3% IR: 1% TOF SIMS: 4% |
| 5 | MPC = 80 mg | Blue, >200 nm, very homogenous | IR: 1% |

The contact angle measurement on different layers (sample 1, 3 and 5) reveals an increasing of the hydrophobic character.

The interest of this monomer mixing is the possibility to adjust with the monomer ratio, the surface energy of the obtained film.

Example 11: Deposition of Poly-MPCDMA/HPMA/TMSPMA Copolymer Thin Films on Stainless Steel in the Presence of 4-Nitrobenzenediazonium Tetrafluoroborate More complex co-polymer can also be obtained as this is illustrated by the following example. In 10 mL of undistilled DMF, containing 21 mg of NaNO3 ($2.5\ 10^{-2}$M as a supporting electrolyte) one introduces 2-methacryloyloxyethyl phosphorylcholine (MPC, 0.1M), dodecyl methacrylate (DMA, 0.1M), hydroxypropylmethacrylate (HPMA, 0.1M) trimethylsilylpropylmethacrylate (TMSPMA, 0.1 M) and 236 mg of 4-nitrobenzenediazonium tetrafluoroborate ($10^{-2}$M). This solution is introduced in a three electrodes cell, the working electrode being a coupon of polished stainless steel, the counter electrode a piece of carbon paper and the reference an Ag/AgCl electrode. The potential of the stainless steel cathode is scanned 20 times from −0.0 V to −2.5 V at a rate of 100 mV/s with Argon bubbling (2 Lmin$^{-1}$).

Based on of the infra-red vibrations characteristics of each monomer, and of the mixture the composition of obtained film is as follows: MPC=25%, DMA=10%, TMSPMA=21%, HPMA not estimated, 4-nitrophenylene not estimated.

TABLE 2

ToF SIMS of the poly-MPC/DMA/HPMA/TMSPMA copolymer thin films on stainless steel

| | Negative ions |
|---|---|
| 85 | $H_2C$=$CH(CH_3)C$(=$O$)$O$ |
| 87 | $CH_2N(CH_3)_3$ |
| 123 | $Si(OCH_3)_3$ + 2 |
| 183 | M(DMA) - $C_{12}H_{25}O$ − 2 |
| 253/255 | M(DMA) −1/+1 |
| | Positive ions |
| 41 | $H_2C$=$CH(CH_3)$ |
| 69 | $H_2C$=$CH(CH_3)C$(=$O$) |
| 86 | $H_2C$=$CH(CH_3)C$(=$O$)$O$ + 1 |
| 121 | $Si(OCH_3)_3$ |
| 166 | $PO_3(CH_2)_2N(CH_3)_3$ |
| 175 | O=CCH=$CHSi(OCH_3)_3$ |
| 184 | $OC_{12}H_{24}$ |
| 227 | $HO(CH_2)_2PO_4(CH_2)_2N(CH_3)_3$ |
| 281 | 296 - $CH_3$ |
| 296 | M(MPC) + 1 |

The structure of the complex nature of the film is confirmed by ToF-SIMS analysis as given in table 2. The ToF-SIMS spectrum indicates, the presence of MPC, DMA and TMSPMA moieties in the copolymer obtained film. HPMA moieties are more difficult to detect as it is the case also for 4-nitrophenylene residues. This later result is not specific to this co-polymer.

Example 12: Electrografting of a Polybutylmethacrylate (Poly-BUMA) Film in the Presence of 4-Diazophenylcarboxylic Acid (DCOOH) Tetrafluoroborate The formation of films of diazo/vinyl is not limited to the 4-nitrobenzene tetrafluoroborate. Another example of diazo derivative which was tested successfully is described below.

A 100 mL solution was prepared from 50 mL DMF (dimethylformamide) and 50 mL BUMA (butylmethacrylate, 0.31M), 211 mg of $NaNO_3$ (25 mM) and 23.6 mg (1 mM) of 4-diazophenylcarboxylic acid (DCOOH) tetrafluoroborate. A polished stainless steel plate carefully cleaned as previously described was introduced ion the electrochemical cell altogether with a piece of carbon paper as the counter electrode and a SCE reference electrode. The potential of the stainless steel cathode was scanned 50 times between open circuit potential and −3V and back at 100 mV/s. The coupon was rinsed with water and then acetone and dried.

A grey film is easily observed on the coupon, it cannot be rubbed out with a finger once dried. Its height is 87±5 nm as measured by profilometry.

The IR spectrum is summarized in Table 3. Assuming that the absorbance of the C=O band of BUMA and DCOOH have similar height, it is possible to estimate that the film contains approximately 30% DCOOH and 70% BUMA.

TABLE 3

ATR IR spectrum of a polybutymethacrylate film

| Wavelength cm$^{-1}$ | Assignment[1,2] |
|---|---|
| 3214 | COOH (DCOOH) |
| 2995-2936 | $CH_3$ stretching (Buma) |
| 2875 | $CH_2$ stretching (Buma) |
| 1727 | C=O stretching (Buma) |
| 1716 shoulder | C=O stretching (DCOOH) |
| 1425 | C—O stretching, (Buma), OH deformation (DCOOH) |
| 1148 | C—O stretching (Buma) |
| 749, 699 | Aromatics CH out of plane (DCOOH) |

[1]DCOOH bands deriving from the diazonium salt, poly-BUMA deriving from the butylmethacrylate.
[2]By comparison with the spectra of polybutylmethacrylate/DCOOH and DCOOH.

The Tof-Sims spectrum is gathered in Table 4.

TABLE 4

ToF-SIMS spectrum of a polybutylmethacrylate/DCOOH film

| m/z | Assignment |
|---|---|
| 41 | $C_2HO^-$ (Buma) |
| 55 | —$CH_2$=$CHCH_2CH_3^-$ or isomer (Buma) |
| 71 | —$OCH_2CH$=$CHCH_3^-$ or isomer (Buma) |
| 73 | —$OBu^-$ (Buma) |
| 85 | —$CH_2$—$C(CH_3)C$(=$O$)$O^-$ (Buma) |
| 183 | $CH_2C(CH_3)(COOBu)CH_2C(CH_3)^-$ (Buma) |
| 269 | $C_{15}H_{25}O_4^-$ (Buma) |
| 76 | —$C_6H_4^-$ (DCOOH) |
| 121 | —$C_6H_4COOH$ (DCOOH) |

Therefore both spectra confirm the presence of polybutylmethacrylate and phenylcarboxylic groups on the film surface.

Example 13: Electrografting of a Polybutylmethacrylate (Buma) Film in the Presence of 4-Diazophenylcarboxylic Acid (DCOOH) Tetrafluoroborate with a Potential Limit at −1V The same procedure as that given in example 12 was employed except that the final potential was limited to −1V. After rinsing with acetone, no film can be observed on the surface, its height cannot be measured (<10 nm).

Figure 3:
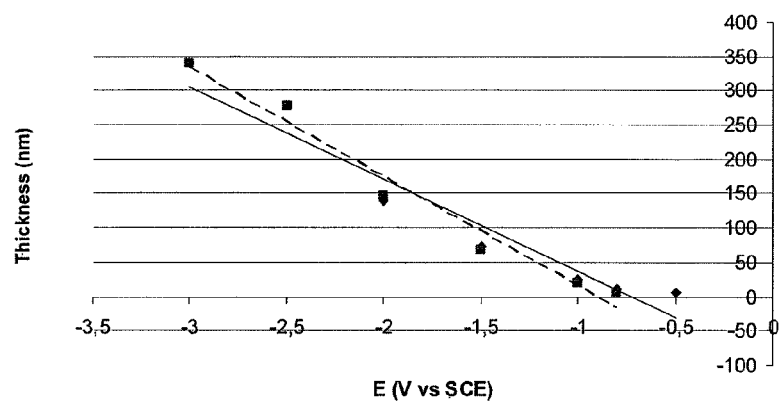
FIG. 3: Thickness of p-BUMA film on 316L as a function of cathodic end potential ($DNO_2$ concentration is $10^{-2}$ mol/l).

Example 14: Dependence of Film Thickness of a Polybutylmethacrylate (Buma) Film on 316L Stainless Steel as a Function of Cathodic Potential The same device setup as that used in example 1 was employed. The concentration of Buma monomer was 3.5 mol/l, the concentration in 4-nitrophenyl diazonium tetrafluoroborate was explored at $10^{-3}$ and $10^{-2}$ mol/l, respectively. The experiments were carried out in DMF as the solvent, under a classical hood. All reagents were used as received without purification nor even water content control. In each experiment, a fresh 316L stainless steel coupon was dipped into the electrolytic solution, and the electrode potential was scanned 50 times between the open circuit potential and −0.8, −1, −1.5, −2, −2.5 and −3 V/SCE, respectively. The coupons were then rinsed 10 min in DMF under ultra-sounds, dried. Their thickness was then measured by profilometry. The results are summarized in the FIGS. 3 and 4:

FIG. 3: Thickness of p-BUMA film on 316L as a function of cathodic end potential ($DNO_2$ concentration is $10^{-2}$ mol/l).

Figure 4:
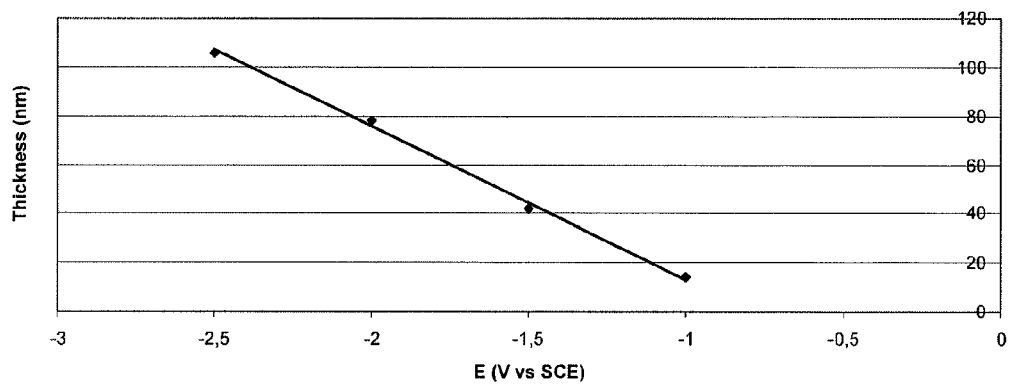
FIG. 4: Thickness of p-BUMA film on 316L as a function of cathodic end potential ($DNO_2$ concentration is $10^{-3}$ mol/l).

FIG. 4:: Thickness of p-BUMA film on 316L as a function of cathodic end potential ($DNO_2$ concentration is $10^{-3}$ mol/l).

These results show that virtually no polymer film (i.e. a film with a thickness which is non detectable by profilometry. The sensitivity of the profilometer as given by the supplier is ca. 5 nm) is formed when the cathodic end potential of the voltamperometric experiment is lower (in absolute value) than −1 V/SCE, which is significantly more cathodic than the reduction potential of the diazonium salt in the same conditions, which is ca.−0.4 V/SCE. This result is obtained both at $10^{-3}$ and at $10^{-2}$ mol/l in diazonium, showing the consistency of the observation.

In particular, one sees that films of the order of a few hundreds of nanometers, which are relevant as Velcro layers for top layers, are obtained only when the scanning protocol has excursions at potentials more cathodic than −2 V/SCE.

Example 15: Quality of a Polybutylmethacrylate (Buma) Film on 316L Stainless Steel as a Function of Cathodic Potential The same device setup and protocols as those used in example 14 were employed. The polymer films were analyzed by IRRAS. The IR spectrum shows a C=O band around 1720 $cm^{-1}$ attributable to the carbonyl group of the Buma polymer, and small $NO_2$ bands around 1345 and 1520 $cm^{-1}$.

One can define a "quality parameter" of the film by estimating the ratio of intensities between the C=O peak and the $NO_2$ peak at 1345 $cm^{-1}$, (C=O)/($NO_2$). The higher the cathodic potential, the larger the rate of electro-reduction of the diazonium salt, which has a reduction potential much less cathodic that any other species in the bath. Thus, one may consider that the content in nitro groups in the film are an indication of the predominance of the electro-reduction of the diazonium and growth of the nitro-phenylenes on themselves, vs the initiation of polymerization reactions of the Buma monomer. This competition is estimated by the (C=O)/($NO_2$) ratio, and as a polymeric p-Buma film is sought for, the higher the ratio the better the film is.

Figure 5:
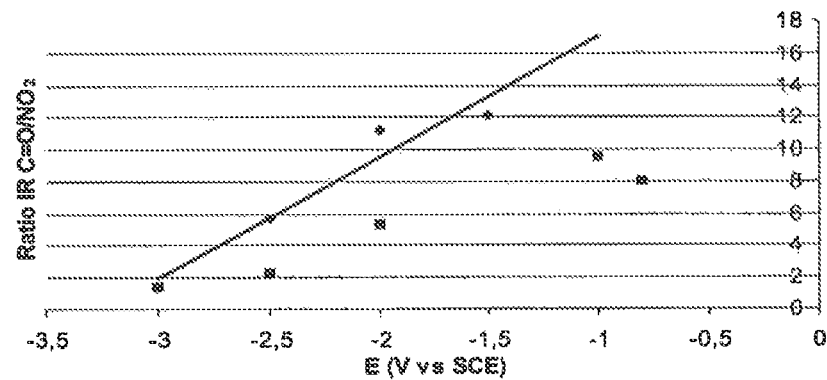
FIG. 5: (C=O)/($NO_2$) (IR) as a function of cathodic end potential. $DNO_2$ concentration is $10^{-2}$ mol/l.
Figure 6:
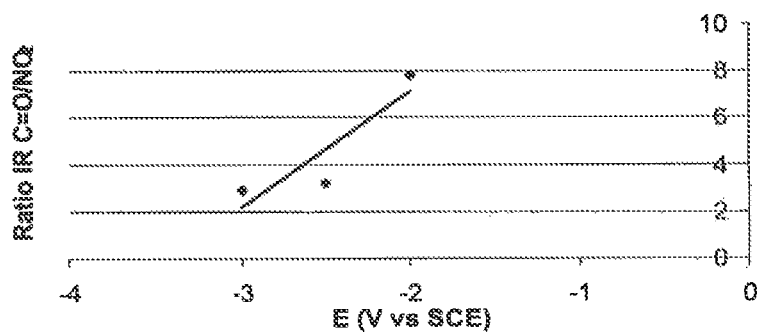
FIG. 6: (C=O)/($NO_2$) (IR) as a function of cathodic end potential. $DNO_2$ concentration is $10^{-3}$ mol/l.

This ratio is shown in the FIGS. 5 and 6 as a function of the cathodic end potential:

FIG. 5: (C=O)/($NO_2$) (IR) as a function of cathodic end potential. $DNO_2$ concentration is $10^{-2}$ mol/l.

FIG. 6: (C=O)/($NO_2$) (IR) as a function of cathodic end potential. $DNO_2$ concentration is $10^{-3}$ mol/l.

These figures show that the best polymeric films (in the sense defined above) are obtained for an excursion in cathodic at about −2 V/SCE. One shall note that this corresponds to the potential range for the reduction of the vinylic monomers themselves. This result also shows that film quality is poor at less cathodic potentials, and very poor at more cathodic potentials.

Example 16: Structure of a Polybutylmethacrylate (Buma) Film on 316L Stainless Steel The same device setup as that used in example 1 was employed. The concentration of Buma monomer was 3.5 mol/l, the concentration in 4-nitrophenyl diazonium tetrafluoroborate was 10-2 mol/l. The experiments were carried out in DMF as the solvent, under a classical hood. All reagents were used as received without purification nor even water content control. The substrate was a 316L stainless steel coupon. It was dipped into the electrolytic solution, and the electrode potential was scanned 3 times between the open circuit potential and −3 V/SCE. The coupons were then rinsed 10 min in DMF under ultra-sounds, dried. An ultra-thin film of the order of 15 nm is obtained, which enables a thorough analysis of surface vs bulk composition of the film by angle resolved XPS. The N1s and C1s spectra are compared when collecting the electrons at close to normal (15°) and grazing (60°) angles, in order to compare the chemical structure of the bulk vs the surface of the polymer film, respectively.

The N1s region of the XPS spectrum shows two major contributions ca. 399.7 and 405.8 eV, stemming from the nitrogen atoms of hydroxylamine or amine groups and from those of nitro groups, respectively (the hydroxylamine or nitro groups are thought to be the result of the reduction of the nitro groups, either during the electrochemical process or under the electron beam during the XPS analysis). The C1s region shows in particular a contribution at 286.2 eV stemming from an aromatic carbon bearing a NO2 or NH2 group, and is thus attributable to the nitrophenyl group obtained by reduction of the diazonium salt.

The comparison of XPS spectra at normal and grazing angles reveal that: (i) aromatic carbons are mostly present at the interface, as their peak is much weaker at grazing angle (=surface); (ii) the overall signal in the N1s region is consistently much weaker at grazing than at normal collection. The ratio between the 399.7 and 405.8 peaks, I(399.7)/I(405.8), is also smaller at grazing angle, indicating that there are comparatively less nitro groups in the vicinity of the metallic surface as compared to the outer surface of the film. This latter result shows that the hydroxylamine and amine groups are most probably stemming from the very electrochemical process, due to the excursion at potentials which are very cathodic which provoke the reduction of the NO2 groups.

On the whole, the results of this example show that the electro-grafted polymeric film is not homogeneous in a direction perpendicular to the surface: close to the metallic surface, the film is richer in nitrophenyl diazonium and its electro-reduction by-products, while farther from the surface, the film is richer in poly-BUMA. This suggests that the electro-grafting takes place primarily via the electro-grafting of the diazoniums, some of the electro-reduction by-products of which are actually starting the polymerization reactions at very cathodic potentials.

Example 17: Deposition of PEG on Stainless Steel in the Presence of 4-Nitrodiazonium Tetrafluoroborate A crosslinkable polyethylene glycol dimethacrylate PEG (875) was used as an illustration of nano-object grafting.

The same procedure as that given in example 1 was used except that poly(ethyleneglycol) dimethacrylate (PEG 875, 50 mL, 0.6M)) was used in place of butylmethacrylate.

On the electrode which is then carefully rinsed DMF, water and air dried is present a 300 nm thick, homogeneous, brownish film.

In the IR spectrum of the film, the carbonyl and the CH2-O vibrations of the PEG are observed at 1729 and 1146 $cm^{-1}$ respectively. The two vibrations of the nitrophenyl group are hardly detectable.

Example 18: Deposition of Poly ϵ-Caprolactone on Stainless Steel in the Presence of 4-Nitrobenzenediazonium Tetrafluoroborate Another class of biopolymers is biodegradable polymers among which many are of natural origin, but polylactones and polylactides (see example 19) constitutes an important class of synthetic biodegradable polymers. Films obtained from ϵ-caprolactone and 4-nitrobenzenediazonium tetrafluoroborate can be obtained in the following procedure.

In 100 ML of undistilled DMF, containing 210 mg of $NaNO_3$ ($2.5 \cdot 10^{-2}$M as a supporting electrolyte) one introduces 55.4 mL of ϵ-caprolactone (5M) and 236 mg of 4-nitrobenzenediazonium tetrafluoroborate. This solution is introduced in a two electrodes cell, the working electrode being a coupon of polished stainless steel and the counter electrode a piece of carbon paper. The potential of the stainless steel cathode is scanned 40 times from −0.15 to −2.8 V at a rate of 100 mV/s with Argon bubbling (2 $Lmin^{-1}$).

The electrode is then carefully rinsed and presents a thick, homogeneous, bluish film.

A blank experiment in absence of diazonium salt does not permit to obtain any film formation.

In the IR spectrum of the film, the carbonyl vibration of the polyester is observed at 1725 $cm^{-1}$ and the two symmetric and antisymmetric vibrations of the nitrophenyl group at 1522 and 1346 $cm^{-1}$, respectively. From the intensity of the bands, one can estimate to about 50% the amount of poly ϵ-caprolactone present in the film.

Example 19: Deposition of Polylactide Thin Films on Stainless Steel in the Presence of 4-Nitrobenzenediazonium Tetrafluoroborate Films obtained from polylactide and 4-nitrobenzenediazonium tetrafluoroborate can be obtained in the following procedure.

A solution is prepared from 100 mL DMSO, 50 g of L-lactide (L-lactide: (3S) cis-3,6-dimethyl 1,4-dioxan 2,5-dione: 3.47 M), 236 mg of 4-nitrobenzene diazonium tetrafluoroborate (0.01M), 210 mg NaNOs (0.025M). The stainless steel cathode is scanned at 0.1V/s between −0.2 and −2.8 V, the solution being deoxygenated and a weak bubbling of nitrogen being maintained in the solution during the electrolysis (2 $Lmin^{-1}$).

A yellow, homogeneous, iridescent, film is observed adherent under rubbing with a finger. The thickness of the film is measured by profilometry at 1.1±0.3 μm.

In the IR spectrum of the film, one observes, both, the signature of the polylactide through the carbonyl band at 1758 $cm^{-1}$ and of the 4-nitropolyphenylene through the $NO_2$ asymmetric and symmetric bands at respectively 1519 and 1346 $cm^{-1}$. From this spectrum, it is possible to estimate a 55% content of polylactide in the film.

The structure is confirmed by ToF-SIMS analysis as given in table 1.

TABLE 5

| ToF-SIMS Spectrum of a polylactide film | |
|---|---|
| m/Z | Attribution |
| 46 | $NO_2^-$ |
| 55, 58 | $CH(CH_3)C(=O) \pm 1$ |
| 71, 73 | $O-CH(CH_3)-C(=O)^- \pm 1$ |
| 87, 89 | $O-CH(CH_3)-C(=O)O \pm 1$ |
| 99, 100 | $C(=O)O-CH(CH_3)C(=O) + $ et $- 1$ |
| 159, 161 | $[O-CH(CH_3-)C(=O)O-CH(CH_3)-C(=O)O^- \pm 1$ |
| 221 | $CH_3SOCH_2C(=O)CH(CH_3)OC(=O)CH(CH_3)O$ |
| 215, 217 | $[O-CH(CH_3)-C(=O)]_3^- \pm 1$ |
| 265, 267 | $NO_2C_6H_4C(=O)CH(CH_3)OC(=OCH(CH_3)O^+ \pm 1$ |
| 358, 361 | $[O-CH(CH_3)-C(=O)]_5^- \pm 1$ |

The ToF-SIMS spectrum indicates, both the presence of polylactide and that of 4-nitrophenylene.

Figure 7:
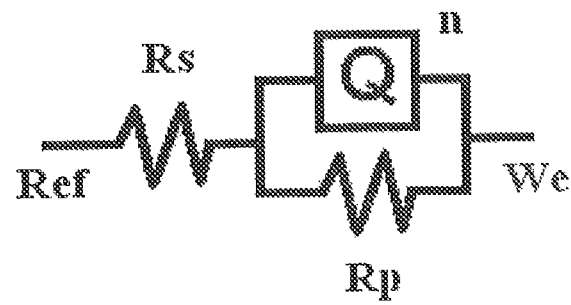
FIG. 7: equivalent electrical circuit. "We" is the working electrode. "Qn" is a constant phase element with 0<n<1, the case n=1 describes an perfect capacitor while the case n=0 describes a pure resistor. "Ref" represents Reference electrode. "Rs" is the electrolyte resistance. "Rp" Is the polarisation resistance of the sample in the electrolyte.

Example 20: Electrochemical Impedance Spectroscopy (EIS) Measurements of a (Water Soluble) Poly-HEMA Film Electro-Grafted on TIN, Showing that the Film is Swollen by Water The EIS spectra are interpreted by using a simple model consisting of the double-layer capacitance in parallel with the polarisation resistance, in addition to the electrolyte resistance. The model can be represented by the equivalent electrical circuit shown FIG. 7, where Rs is the electrolyte resistance, Rp is the polarisation resistance of the sample in the electrolyte. Q is the constant phase element; it is used instead of a capacitance to account for the non-ideal capacitive response stemming from the presence of diffusion phenomena in the vicinity of the electrode (see for example: C. Gabrielli. Technical Report. Intro Elect. Imp. Tech. CSB/AO1 (1990), Edt. Schlumberger Technologies Instrument Division Farnborough. Hampshire. England.)

Both the characteristics of the constant phase element and the polarisation resistance give indication on how much the diffusion and thus ionic conduction are being modified in the vicinity of the surface upon coating it with an electro-grafted HEMA layer. We have found it more convenient to make this follow up by evaluating how much the polarisation resistance is modified upon grafting.

Figure 8:
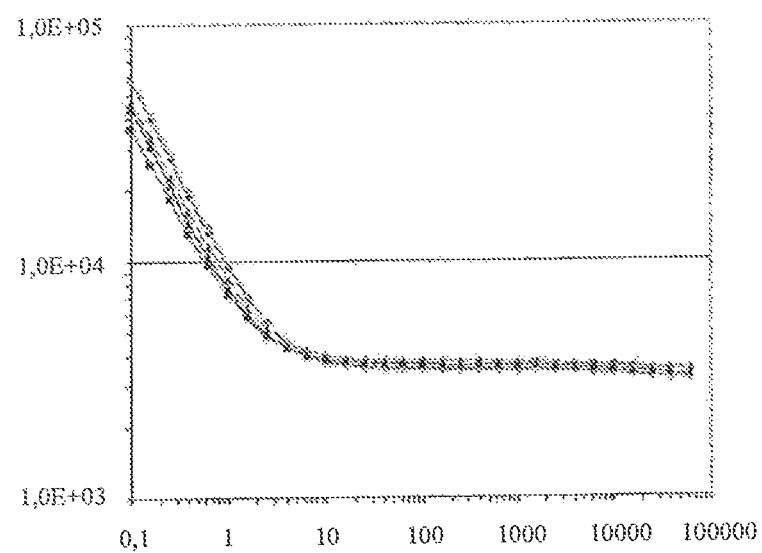
FIG. 8: Comparison of impedance moduli of a bare TiN coupon to that of a coupon coated with a layer of HEMA/ 4-nitrophenyldiazonium tetrafluoroborate, and to that of the same coated coupon after drying for 24 h at 30° C. under reduced pressure. Abscissa: Frequency (Hertz); Ordinate: module (Ohm·cm²)
Figure 9:
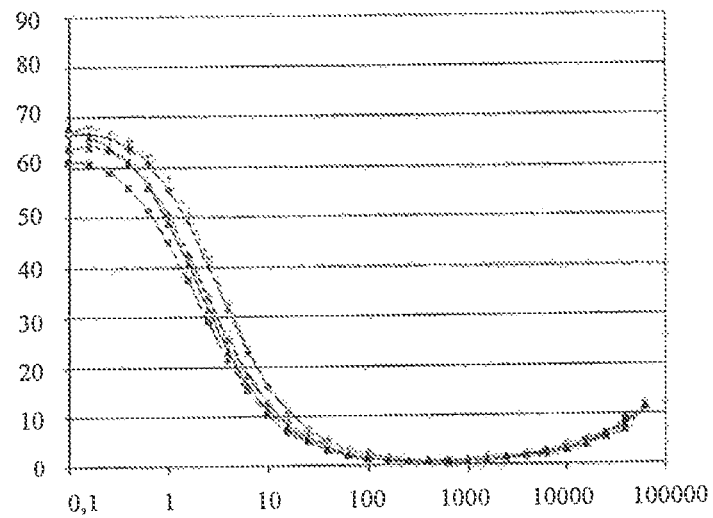
FIG. 9: Comparison of phase angles of a bare TiN coupon to that of a coupon coated with a layer of HEMA/4-nitrophenyldiazonium tetrafluoroborate, and to that of the same coated coupon after drying for 24 h at 30° C. under reduced pressure. Abscissa: Frequency (Hertz); Ordinate: phase angle (degree)

Typical spectra giving the modulus (Z) and phase angle as a function of sampling frequency are given in FIGS. 8 and 9.

FIG. 8: Comparison of impedance moduli of a bare TiN coupon to that of a coupon coated with a layer of HEMA/4-nitrophenyldiazonium tetrafluoroborate, and to that of the same coated coupon after drying for 24 h at 30° C. under reduced pressure. Abscissa: Frequency (Hertz); Ordinate: module (Ohm·$cm^2$)

FIG. 9: Comparison of phase angles of a bare TiN coupon to that of a coupon coated with a layer of HEMA/4-nitrophenyldiazonium tetrafluoroborate, and to that of the same coated coupon after drying for 24 h at 30° C. under reduced pressure. Abscissa: Frequency (Hertz); Ordinate: phase angle (degree)

These highlight that the fact of coating the TiN surface with an HEMA/4-nitrophenyldiazonium tetrafluoroborate polymer layer only has a slight influence over the global impedance of the electrode. One shall note that the same spectra have also been recorded after drying the coated electrodes for 24 h at 30° C. at 700 mbar reduced pressure in a vacuum oven: FIGS. 8 and 9 show that the impedance remains identical, evidencing that the swelling of the HEMA/4-nitrophenyldiazonium tetrafluoroborate films on the electrodes is reversible.

To make this comparison quantitative, we have extracted the electrical parameters of FIG. 8 by performing a numerical non linear least square fit of the experimental data of FIG. 9. Typical results of spectra fitting are given in table 6.

TABLE 6

Fitting results for the TiN material samples

| Sample | $Rp$ (Ohm · cm$^2$) × 10$^{-5}$ |
|---|---|
| Bare TiN | 4.10 |
| TiN after HEMA/4-nitropheny diazonium tetrafluoroborate film deposition | 3.91 |

The percentage of variation Δ of the polarisation resistance is given by:

$$\Delta = \left(1 - \frac{R_{bare\,TiN}}{R_{TiN\,after\,eG\,HEMA}}\right) \times 100\% = \left(1 - \frac{3.91.10^5}{4.1.10^5}\right) \times 100 = 46\%$$

After coating the TiN electrode with an electrografted with a HEMA/4-nitrophenyldiazonium tetrafluoroborate film according to the present invention, the low polarisation resistance very slightly differs from that of the bare TiN coupon. This argument indicates that the polymer is not an electrical insulator i.e. that it is permeable to the ions and consequently is perfectly swollen by the electrolyte.

Even though it is fully swollen by the electrolyte, the HEMA/4-nitrophenyldiazonium tetrafluoroborate film does not dissolve in water, which is a good indication in favour of the strong grafting of said film onto the TiN surface.

Example 21: The Grafted Polymer Layers can be Used as Adhesion Primers for Much Thicker Layers Sprayed Over them A 7×1 cm×1 mm electropolished, dog-bone shaped, 316L stainless steel coupon is uniformly coated with a poly-BUMA electro-grafted layer according to the protocol given in example 1. The film has a thickness of 150 nm.

The middle (thinner) part of the coupon is coated on one side with 5 μm of PLA (polylactide acid) by spray. This is achieved by masking the two wider extremities of the dog-bone shaped coupon and spraying it with a solution of PLA in chloroform (3% w/w). The coupon is vacuum dried until constant mass. Four small dots are drawn with an ink pen on top of the PLA layer.

Figure 10:
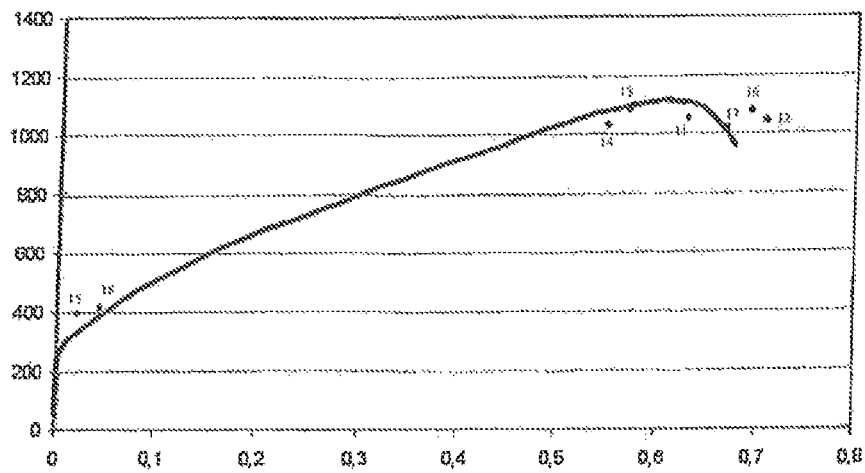
FIG. 10: corrected strain/stress response of the coupon in the INSTRON machine; with and without a poly-BUMA electro-grafted underlayer. Abscissa: true deformation; Ordinate: true strain/stress (MPa)

The coupon is then placed in an INSTRON (5 kN capacity, ε'=10–3 s$^{-1}$) machine and pulled apart at the two edges. The deformation of the dots on the surface is followed by a video camera which informs as to the deformation speed of the dots is identical to that imposed by the INSTRON machine. In case it is not, then it means that some delamination is occurring within the sandwich layer:

FIG. 10 shows the corrected strain/stress response of the coupon in the INSTRON machine and compares with and without a poly-BUMA electro-grafted underlayer. The black curve is identical for all trials, with or without electro-grafted layer, and shows the elastic, inelastic and breaking regimes of the metallic coupon itself, which is little affected by the overall 5 μm coating.

The numbered dots on the curve are indicative of the information given by the camera while the test is being performed, and more precisely indicative of when the camera detects that delamination is occurring.

The result of the test is that without electro-grafted underlayer, the PLA layer delaminates on 316L stainless steel for moderate stress and strain (points #15 and 18 in FIG. 10), while the sandwich actually never delaminates, up to the rupture of the metal, when an electro-grafted layer of BUMA is used as the underlayer (points #11, 12, 13, 14, 16, 17 in FIG. 17-2).

This shows the significant improvement achieved by the electro-grafted layer according to the present invention, even though it is very thin as compared to the 5 μm layer which sits on top of it.

The invention claimed is:
1. A biocompatible object comprising:
   a surface, or a portion of a surface, which is electrically conductive or semi conductive;
   an organic film allowing ionic conduction, electro-grafted on said surface, or portion of said surface, by electro-reduction of a solution comprising at least one diazonium salt, glycerol, and at least one monomer or macro-object comprising a group that can be involved in propagation chain reactions and which is precursor of said organic film.
2. The object of claim 1, wherein said solution comprises at least one diazonium salt and at least one macro-object which is a polymeric or nonpolymeric macrostructure functionalized with at least one group that can be involved in propagation chain reactions.
3. The object of claim 1, wherein said group is a vinylic group or a cyclic molecule cleavable by nucleophilic attack.
4. The object of claim 3, wherein said cyclic molecule has formula (II):

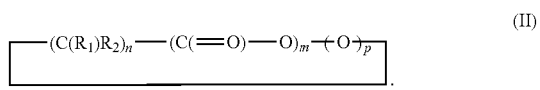

(II)

in which:
   R1 and R2, identical or different, represent a hydrogen atom; a C1-C4 alkyl group; a nitrile group; a function selected from the group consisting of hydroxyl, amine —NHx with x=1 or 2, ammonium, thiol, carboxylic acids and their salts, ester, amide —C(═O)NHy in which y=1 or 2, imide, imidoester, acid halide C(═O)X in which X represents an halogen atom selected from fluorine, chlorine, bromine and iodine, an acid anhydride —C(═O)OC(═O), amino acids, phosphonic acids and their salts, phosphoric acids and their salts, phosphonyl choline and its derivatives, sulfonic acids and their salts, sulfuric acids and their salts, nitrile, succinimide, phthalimide, isocyanate, epoxy, siloxane —Si(OH)z in which z is a whole number ranging between 1 and 3 inclusively, benzoquinone, carbonyl-diimidazole, para-toluene sulphonyl, para-nitrophenyl chloroformiate, ethylene and vinyl, aromatic; a functional group being able to complex cations; molecular structures substituted and/or functionalized starting from these functional groups; thermally or photochemically cleavable groups; electroactive groups, aniline, thiophene, methylthiophene, bis thiophene, pyrrole, ethylene dioxothiophene (EDOT), as well as electro-cleavable groups, as well as mixtures of monomers containing the aforementioned groups;

the straight line of formula (II) represents an C3-C10 alkyl radical; and n, m and p, identical or different, are whole numbers ranging between 0 and 20 inclusively, under the proviso that n, m and p are not at the same time 0.

5. The object of claim 3, wherein said cyclic molecule is selected from epoxies, lactones, lactic acids, glycolic acids, oxiranes, polyaspartate and their mixtures.

6. The object of claim 3, wherein said vinylic group is selected from the group consisting of methacrylate, acrylate, vinyl chloride, acrylonitrile, methacrylonitrile, 4-vinylpyridine, 2-vinylpyridine, and N-vinylpyrrolidone.

7. The object of claim 1, wherein said macro-object is selected from compounds of formula:

A-P

A-P—B

P(A)n

[M(A)]n

A-[M(B)]n

A-[M(B)]n-C

A-P-[M(B)]n

A-P-[M(B)]—C in which:
(i) P is a macrostructure selected from: organic or inorganic oligomers and polymers, polymers obtained by polycondensation of one or more reagents, polysiloxanes, poly(orthoesters), polyphosphates, parylene and substituted parylene-based polymers, conducting polymers, oligopeptides and proteins, nucleic acid molecules, polysaccharides, substituted or unsubstituted porphyrins, substituted or unsubstituted phthalocyanins, polymers formed from substituted monomers or from substituted macromolecules from the list above, prepolymers, macromers or telechelics based on the monomers and/or macromolecules from the list above, copolymers and/or mixtures which can be formed from these polymers, from their constituent monomers or from the macromolecules above, which may or may not be substituted;
(ii) n is an integer greater than or equal to 1;
(iii) M is a constituent monomer unit of the structures of type P defined above when said structures are a polymer;
(iv) A, B and C, which may be identical or different, are selected from chain polymerizable groups selected from vinylic groups and cleavable cyclic molecules, A, B and C being linked via covalent, ionic or oxidative bonds, or via hydrogen bonding, with the macrostructural portion P or the monomeric portion M.

8. The object of claim 1, wherein said surface is a surface of stainless steel, cobalt or its alloys, titanium or its alloys, biomed, iron, copper, nickel, niobium, aluminum, silver, silicon (doped or not), silicon carbide, titanium nitride, tungsten, nitride of tungsten, tantalum, nitride of tantalum or a noble metal surface selected from platino-iridium or iridium, platinum, gold surfaces.

9. The object of claim 1, wherein said diazonium salt is aryldiazonium salt.

10. The object of claim 1, wherein said electro-reduction is performed in an electrolysis cell using the conducting or semiconducting surface to be coated as working electrode and at least one counterelectrode, so as to result, by application of at least one protocol consisting of an electrical polarization of the surface by applying a variable potential over at least a range of values which are more cathodic than the reduction or peak potential of all diazonium salts in the said solution, in a grafted coating of said organic film on said surface.

11. The object of claim 1, wherein said organic film has a thickness ranging from 10 nm to 10 μm.

12. The object of claim 1, wherein the object is a stent.

13. The object of claim 1, wherein the solution comprising at least one diazonium salt and at least one monomer bearing at least one chain polymerizable functional group and which is precursor of said organic film.

14. The object of claim 13, wherein said monomer is an activated vinyl monomer of formula (I):

$$H_2C=\overset{A}{\underset{B}{\bigg|}} \quad (I)$$

in which:
A, B, are identical or different, and represent a hydrogen atom; a C1-C4 alkyl group; a nitrile group; a function selected from the group consisting of hydroxyl, amine —NHx with x=1 or 2, ammonium, thiol, carboxylic acids and their salts, ester, amide —C(=O)NHy in which y=1 or 2, imide, imidoester, acid halide C(=O)X in which X represents an halogen atom selected among fluorine, chlorine, bromine and iodine, an acid anhydride —C(=O)OC(=O), amino acids, phosphonic acids and their salts, phosphoric acids and their salts, phosphonyl choline and its derivatives, sulfonic acids and their salts, sulfuric acids and their salts, nitrile, succinimide, phthalimide, isocyanate, epoxy, siloxane —Si(OH)z in which z is a whole number ranging between 1 and 3 inclusive, benzoquinone, carbonyl-diimidazole, para-toluene sulphonyl, para-nitrophenyl chloroformiate, ethylene and vinyl, aromatic; a functional group being able to complex cations; molecular structures substituted and/or functionalized starting from these functional groups; thermally or photochemically cleavable groups; electroactive groups, aniline, thiophene, methylthiophene, bis thiophene, pyrrole, ethylene dioxothiophene (EDOT) as well as electro-cleavable groups, as well as mixtures of monomers containing the aforementioned groups.

15. The object of claim 1, wherein said monomer is a cyclic molecule cleavable by nucleophilic attack of formula (II):

$$\boxed{-(C(R_1)R_2)_n-(C(=O))-O)_m-(O)_p} \quad (II)$$

in which:
R1 and R2, identical or different, represent a hydrogen atom; a C1-C4 alkyl group; a nitrile group; a function selected from the group consisting of hydroxyl, amine —NHx with x=1 or 2, ammonium, thiol, carboxylic acids and their salts, ester, amide —C(=O)NHy in which y=1 or 2, imide, imido-ester, acid halide C(=O)X in which X represents an halogen atom chosen among fluorine, chlorine, bromine and iodine, an acid anhydride —C(=O)OC(=O), amino acids, phosphonic acids and their salts, phosphoric acids and their salts, phosphonyl choline and its derivatives, sulfonic acids and their salts, sulfuric acids and their salts, nitrile, succinimide, phthalimide, isocyanate, epoxy, siloxane —Si(OH)z in which z is a whole number ranging between 1 and 3 inclusively, benzoquinone, carbonyl-diimidazole, para-toluene sulphonyl, para-nitrophenyl chloroformate, ethylene and vinyl, aromatic; a functional group being able to complex cations; molecular structures substituted and/or functionalized starting from these functional groups; thermally or photochemically cleavable groups; electroactive groups, aniline, thiophene, methylthiophene, bis thiophene, pyrrole, ethylene dioxothiophene (EDOT), as well as electro-cleavable groups, as well as mixtures of monomers containing the aforementioned groups;

the straight line of formula (II) represents an C3-C10 alkyl radical; and n, m and p, are identical or different, and are whole numbers ranging between 0 and 20 inclusively, under the proviso that n, m and p are not at the same time 0.

16. The object of claim 1, wherein the macro-object is a polymeric or non-polymeric macrostructure linked to at least one chain polymerizable functional group.

17. The object of claim 16, wherein the link between the macrostructure and the chain polymerizable group is a covalent bond.

18. The object of claim 16, wherein the link between the macrostructure and the chain polymerizable group is an ionic bond.

19. The object of claim 16, wherein the link between the macrostructure and the chain polymerizable group is an oxidative bond.

20. The object of claim 16, wherein the link between the macrostructure and the chain polymerizable group is a hydrogen bond.

21. The object of claim 3, wherein the vinyl group comprises activated vinyl monomers.

22. The object of claim 21, wherein the vinyl monomer is activated by electron withdrawing groups.

23. The object of claim 22, wherein the activated vinyl monomers have the formula (I):

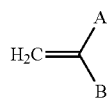

(I)

in which:

A and B identical or different, are chosen from the group consisting of a hydrogen atom; a C1-C4 alkyl group; a nitrile group; a selected organic function among the functions hydroxyl, amine: NHx with x=1 or 2, ammonium, thiol, carboxylic acids and their salts, ester, amide: C(=O)NHy in which y=1 or 2, imide, imido-ester, acid halide; C(=O)X in which X represents an halogen atom selected from fluorine, chlorine, bromine and iodine, acid anhydride: —C(=O)OC(=O), amino acids, phosphonic acids and their salts, phosphoric acids and their salts, phosphonyl choline and its derivatives, sulfonic acids and their salts, sulfuric acids and their salts, nitrile, succinimide, phthalimide, isocyanate, epoxy, siloxane: —Si(OH)z in which z is a whole number ranging between 1 and 3 inclusively, benzoquinone, carbonyl-diimidazole, para-toluene sulphonyl, para-nitrophenyl chloroformate, ethylene and vinyl; a functional group being able to complex cations; molecular structures substituted and/or functionalized starting from these functional groups; thermally or photochemically cleavable groups; electroactive groups as well as electro-cleavable groups, as well as mixtures of monomers containing the aforementioned groups.

24. The object of claim 21, wherein the activated vinylic monomer is selected from the group consisting of acrylonitrile, methacrylonitrile, methyl ethyl, propyl and butyl methacrylate, hydroxyethyl hydroxypropyl glycidyle methacrylate, acrylamides, cyanoacrylates, di-acrylates or di-methacrylates, tri-acrylates or tri-methacrylates, tetra-acrylates or tetra-methacrylates, acrylic and methacrylic acid, styrene and its derivatives, parachlorostyrene, pentafluorostyrene, N-vinyl pyrrolidone, 2-vinyl pyridine, vinyl acryloyle, methacryloyle halides, and di-vinylbenzene (DVB).

25. The object of claim 2, wherein the macro-object is any crosslinked or non-crosslinked polymer functionalized at the end of or along its chain by activated vinyl groups or by cyclic groups.

26. The object of claim 2, wherein the macro-object is any crosslinked polymer functionalized in crosslinking zones by activated vinyl groups or by cyclic groups.

27. The object of any of claim 25 or 26, wherein the polymer is a homopolymer.

28. The object of any of claim 25 or 26, wherein the polymer is selected from the group consisting of poly-acrylonitrile, poly-methacrylonitrile, poly-methyl methacrylate, poly-ethyl methacrylate, poly-propyl methacrylate, poly-butyl methacrylate, poly-hydroxyethyl methacrylate, poly-hydroxylpropylmethacrylate, poly-cyanoacrylates, poly-acrylic acid, poly-methacrylic acid, poly-styrene and of its derivatives, poly-N-vinylpyrrolidone, poly-vinyl halides, polyacrylamides; poly-isoprene, poly-ethylene, poly-propylene, poly-ethylene oxide, polylactones poly-lactides, poly-glycolides poly-ethylene glycol, polyamides, polyurethanes, poly(orthoesters), polyaspartates, poly-aniline, poly-thiophene, poly-ethylenedioxythiophene (EDOT), poly-pyrrole, or their substituted derivatives.

29. The object of claim 2, wherein the macro-object is any macromolecule partially or totally functionalized by activated vinyl groups or by cyclic groups.

30. The object of claim 29, wherein the macromolecule is protein.

31. The object of claim 30, wherein the protein is selected from the group consisting of antigens, enzymes, growth factors, antibodies and collagens.

32. The object of claim 29, wherein the macromolecule is nucleic acid.

33. The object of claim 32, wherein the nucleic acid is selected from the group consisting of single- and double-stranded DNA, and single- and double-stranded RNA.

34. The object of claim 29, wherein the macromolecule is polysaccharides.

35. The object of claim 34, wherein the polysaccharide is selected from the group consisting of cellulose, substituted celluloses, chitosans, substituted or functionalized chitosans, dextrans and substituted or functionalized dextrans, amyloses, pectins, starch and heparin.

36. The object of claim 2, wherein the macro-object is any object of nanometric or micrometric size, the surface of which is capable of being functionalized with activated vinyl groups or cyclic groups.

37. The object of claim 35, wherein the object is mineral aggregates.

38. The object of claim 35, wherein the mineral aggregates are selected from the group consisting of beads of silica, oxides, nanobeads, nanotubes, fullerenes, lipid vesicles, liposomes and niosomes, and living cells.

39. The object of claim 1, wherein the surface is selected from a group consisting of metal, organic or mineral surfaces, wood, glass, plastic, plant fibers, keratin materials, organic or gels, composites thereof or mixtures thereof.

40. The object of claim 1, wherein the diazonium salt has general formula R—N2+, X−, in which:

R comprises an organic or mineral group selected from the group consisting of: nitro, fluoro, bromo, chloro, iodo, thiocyanato, sulphate, sulphonate, sulphonium salts, phosphate, phosphonate, phosphonium salts, diazonium salts, amine, ammonium, alcohol, aldehyde, ketone, carboxylic acid, ester, amide, nitrile, anhydride, acid halide, alkyl, alkenyl, alkynyl, aryl, naphthyl, anthryl, pyrryl and polyaromatic groups of higher degree, and wherein the alkyl, alkenyl, alkynyl, aryl, naphthyl, anthryl, pyrryl and polyaromatic groups of higher degree include a group selected from the group consisting of: nitro, fluoro, bromo, chloro, iodo, thiocyanato, sulphate, sulphonate, sulphonium salts, phosphate, phosphonate, phosphonium salts, diazonium salts, amine, ammonium, alcohol, aldehyde, ketone, carboxylic acid, ester, amide, nitrile, anhydride, and acid halide, X− is an anion selected from the group consisting of: halogens, sulphates, phosphates, perchlorates, tetrafluoroborates, hexafluorophosphates and carboxylates.

41. The object of claim 1, wherein the diazonium salt is an aryl diazonium salt with a formula ArN2+, X−, in which Ar represents an aromatic group and X represents an anion selected from the group consisting of: halogens, sulphates, phosphates, perchlorates, tetrafluoroborates, hexafluorophosphates and carboxylates.

42. The object of claim 41, wherein the aryl group moiety is selected from the group consisting of one or more aromatic groups linked together or fused, a C6-C14 aromatic moiety substituted by one or more functional substituents or a heteroaromatic moiety having from 4 to 14 atoms, optionally_ substituted by one or more functional substituents with one or more heteroatoms selected from a group consisting of oxygen, nitrogen, sulphur or phosphorus.

43. The object of claim 42, wherein the aryl group comprises one or more substituents selected from the group consisting of:

aliphatic radicals, linear or ramified from 1 to 20 carbon atoms optionally comprising one or more double or triple bond, optionally substituted by carboxyl radicals, $NO_2$, protected disubstituted and monosubstituted amino groups, cyano, diazonium, alkoxy containing from 1 to 20 carbon atoms, alkoxycarbonyl containing from 1 to 20 carbon atoms, alkylcarbonyloxy containing from 1 to 20 carbon atoms, optionally fluorinated vinyl or allyl, the halogen atoms;

radicals aryls optionally substituted by carboxyls, $NO_2$, cyano, diazonium, alkoxy containing from 1 to 20 carbon atoms, alkoxycarbonyl containing from 1 to 20 carbon atoms, alkylcarbonyloxy containing from 1 to 20 carbon atoms, possibly fluorinated vinyl or allyl, the halogen atoms;

radicals carboxyls, $NO_2$, protected disubstituted, monosubstituted amino groups amido, cyano, diazonium, sulphonic, phosphonic, alkoxy containing from 1 to 20 carbon atoms, alkoxycarbonyl containing from 1 to 20 carbon atoms, alkylcarbonyloxy containing from 1 to 20 carbon atoms, optionally fluorinated vinyl, the halogen atoms.

44. The object of claim 43, wherein the substituents of the aryl group have reactive functions that are capable of reacting with the chemical functions carried by other molecules after one or more chemical transformations.

45. The object of claim 44, wherein the reactive functions carried by the aryl group are the allyl or vinyl or acetylenic functions, the halogens, alcohols, the anhydrides or halides of acid, the nitriles, the isocyanates, the amines, sulphonic acids or sulphonates, phosphonic acids or phosphonates.

46. The object of claim 1, wherein the solution comprises additional spectator for solubilizing the monomers, wherein the spectator does not intervene in the electropolymerisation reaction.

47. The object of claim 46, wherein the spectator compound is a solvent.

48. The object of claim 46, wherein the spectator compound is a solvent of the organic film.

49. The object of claim 47 or 48, wherein the solvent is selected from the group consisting of water, ethanol, other alcohols, dimethylformamide, dimethylsulfoxide, ethyl acetate, acetonitrile, tetrahydrofuran, propylene carbonate and chlorinated solvents.

50. The object of claim 1, wherein the solution comprises a supporting electrolyte.

51. The object of claim 50, wherein the supporting electrolyte is selected from the group consisting of quaternary ammonium salts, sodium nitrate and sodium chloride.

52. The object of claim 1, wherein the organic film can be swollen by a solvent.

53. The object of claim 1 further comprising an outer coating.

54. The object of claim 53, wherein the outer coating is applied by electro-deposition or by another means.

55. The object of claim 1 further comprising a functional layer that is deposited into the electro-grafted layer through interdigitation.

56. The object of claim 55, wherein the functional layer has a thickness of 10 nanometers to 5 micrometers.

57. The object of claim 55, wherein the conductive surface is a 316 stainless steel coupon, the grafted polymer layer is a 150 nm poly-BUMA layer, electro-grafted on a 316L stainless steel coupon, and the functional layer is a 5 micrometer PLA layer.

58. The object according to claim 14, wherein the monomer is butyl methacrylate, the activated vinyl monomer of formula (I) wherein A is $C_1$-alkyl and B is an ester.

59. The object of claim 14, wherein the aromatic is selected from the group constituting of toluene, benzene, halogeno-benzene, pyridine, pyrimidin, styrene or halogeno-styrene and their substituted equivalents.

60. The object of claim 14, wherein the thermally or photochemically cleavable groups are selected from the group constituting of diazonium salts, peroxides, nitrenes, azides, nitroso anilides, alkoxyamines, benzophenone and its derivatives, dithioesters, dithiocarbamates and trithiocarbonates.

61. The object of claim 60, wherein the alkoxyamine is 2,2,6,6-tetramethyl-1-piperidinyloxy (TEMPO).

62. The object of claim 14, wherein the electro-cleavable groups is selected from the group constituting of diazonium, sulfonium, phosphonium and iodonium salts.

63. The object of claim 23, wherein the aromatic is selected from the group constituting of toluene, benzene, halogeno-benzene, pyridine, pyrimidin, styrene or halogeno-styrene and their substituted equivalents.

64. The object of claim 23, wherein the functional group being able to complex cations is a reducible cation of metals selected from the group constituting of copper, iron and nickel.

65. The object of claim 23, wherein the thermally or photochemically cleavable groups are selected from the group constituting of diazonium salts, peroxides, nitrenes, azides, nitroso anilides, alkoxyamines, benzophenone and its derivatives, dithioesters, dithiocarbamates and trithiocarbonates.

66. The object of claim 65, wherein the alkoxyamine is 2,2,6,6-tetramethyl-1-piperidinyloxy (TEMPO).

67. The object of claim 23, wherein the electroactive groups is a conducting polymer precursor selected from the group constituting of aniline, thiophene, methylthiophene, bis thiophene, pyrrole, ethylene dioxothiophene and (EDOT).

68. The object of claim 23, wherein the electro-cleavable group is selected from the group constituting of diazonium, sulfonium, phosphonium and iodonium salts.

69. The object of claim 24, wherein the acrylamide is selected from the group constituting of amino-ethyl, propyl, butyl, pentyl and hexyl methacrylamides.

70. The object of claim 24, wherein the tetra-methacrylate is pentaerythritol tetramethacrylate.

71. The object of claim 24, wherein the activated vinylic monomer is selected from the group consisting of vinyl or methacrylate or acrylate based crosslinking agents and their derivatives.

72. The object of claim 45, wherein the alcohols are of type —(CH2)n-CH2OH, the carboxylic acids of type —(CH2)n-COOH, the amines are of type —(CH2)n-NH2 and n is an integer number between 0 and 10.

73. The object of claim 51, wherein the quaternary ammonium salts are selected from the group consisting of perchlorates, tosylates, tetrafluoroborates, hexafluorophosphates and quaternary ammoniums halides.

74. The object of claim 73, wherein the perchlorate is selected from the group consisting of tetraethylammonium perchlorate (TEAP), tetrabutylammonium perchlorate (TBAP), tetrapropylammonium perchlorate (TPAP) and benzyltrimethylammonium perchlorate (BTMAP).

75. The object of claim 52, wherein the solvent is water.

76. The object of claim 54, wherein the another mean is selected from the group consisting of dip coating, spray coating and spin coating.

77. The object of claim 4, wherein the aromatic is selected from the group constituting of toluene, benzene, halogeno-benzene, pyridine, pyrimidine, styrene or halogeno-styrene and their substituted equivalents.

78. The object of claim 4, wherein the thermally or photochemically cleavable groups are selected from the group constituting diazonium salts, peroxides, nitrenes, azides, nitroso anilides, alkoxyamines, benzophenone and its derivatives, dithioesters, dithiocarbamates and trithiocarbonates.

79. The object of claim 78, wherein the alkoxyamine is 2,2,6,6-tetramethyl-1-piperidinyloxy (TEMPO).

80. The object of claim 78, wherein the electro-cleavable group is selected from the group consisting of diazonium, sulfonium, phosphonium and iodonium salts.

81. The object of claim 7, wherein the cleavable cyclic molecules are selected from the group consisting of lactones, lactides, and oxiranes.

82. The object of claim 15, wherein the aromatic is selected from the group constituting of toluene, benzene, halogeno-benzene, pyridine, pyrimidin, styrene or halogeno-styrene and their substituted equivalents.

83. The object of claim 15, wherein the thermally or photochemically cleavable groups is selected from the group constituting of diazonium salts, peroxides, nitrenes, azides, nitroso anilides, alkoxyamines, benzophenone and its derivatives, dithioesters, dithiocarbamates and trithiocarbonates.

84. The object of claim 15, wherein the electro-cleavable group is selected from the group consisting of diazonium, sulfonium, phosphonium and iodonium salts.

85. The object of claim 24, wherein the acrylamide group is selected from the group consisting amino-ethyl, propyl, butyl, pentyl and hexyl methacrylamides.

86. The object of claim 24, wherein the activated vinylic monomer is selected from the group consisting of vinyl, methacrylate, acrylate based crosslinking agents and their derivatives.

87. The object of claim 83, wherein the alkoxyamine is 2,2,6,6-tetramethyl-1-piperidinyloxy (TEMPO).

88. The object of claim 28, wherein the poly-lactone is poly-epsilon-caprolactone, the poly-lactide is poly-lactic acid and the poly-glycolide is poly-glycolic acid.

89. The object according to claim 21, wherein the monomer is butyl methacrylate, the activated vinyl monomer of formula (I) wherein A is $C_1$-alkyl and B is an ester.

* * * * *